US012686843B2

(12) United States Patent
Tandon et al.

(10) Patent No.: US 12,686,843 B2
(45) Date of Patent: Jul. 21, 2026

(54) END-TO-END CELL THERAPY BIOPROCESSING DEVICE FOR CONTINUOUS-FLOW ENRICHMENT, WASHING, AND ELECTROTRANSFECTION OF TARGET CELLS

(71) Applicant: The Charles Stark Draper Laboratory, Inc., Cambridge, MA (US)

(72) Inventors: Vishal Tandon, Somerville, MA (US); Jeffrey Borenstein, West Roxbury, MA (US); Jason Fiering, Somerville, MA (US); Jenna Balestrini, Boston, MA (US); Heena Mutha, Somerville, MA (US); Jonathan Robert Coppeta, Windham, NH (US); Mark Mescher, West Newton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1150 days.

(21) Appl. No.: 17/100,379

(22) Filed: Nov. 20, 2020

(65) Prior Publication Data

US 2021/0155889 A1     May 27, 2021

Related U.S. Application Data

(60) Provisional application No. 62/939,191, filed on Nov. 22, 2019.

(51) Int. Cl.
*C12M 1/42* (2006.01)
*B01L 3/00* (2006.01)
(Continued)

(52) U.S. Cl.
CPC ....... *C12M 35/02* (2013.01); *B01L 3/502761* (2013.01); *B01L 3/502776* (2013.01);
(Continued)

(58) Field of Classification Search
None
See application file for complete search history.

(56) References Cited

U.S. PATENT DOCUMENTS

| | | |
|---|---|---|
| 2004/0069717 A1 | 4/2004 | Laurell et al. |
| 2008/0217259 A1* | 9/2008 | Siversson ............ B01D 21/283 |
| | | 210/542 |

(Continued)

FOREIGN PATENT DOCUMENTS

| | | | |
|---|---|---|---|
| CN | 109715124 A | 5/2019 | |
| JP | 2019-527536 A | 10/2019 | |
| WO | WO-2018022158 A1 * | 2/2018 | ............. A61K 35/17 |

OTHER PUBLICATIONS

Longsine-Parker, et al. "Microfluidic electro-sonoporation: a multi-modal cell poration methodology through simultaneous application of electric field and ultrasonic wave". Lab on a Chip. 2013. 13, 2144. (Year: 2013).*

(Continued)

*Primary Examiner* — Michael A Marcheschi
*Assistant Examiner* — Nathan G Esperon
(74) *Attorney, Agent, or Firm* — BROOKS KUSHMAN P.C.

(57) ABSTRACT

A system for cell bioprocessing and cell therapy manufacturing can include a series of microfluidic modules to enable continuous-flow end-to-end cell bioprocessing. Each module can implement a different technology, and the modules can be coupled to one another to perform various unit operations in the cell bioprocessing or cell-therapy manufacturing chain to enable direct processing of a blood or blood product sample. The system can automatically and continuously process the sample into genetically-modified lymphocytes or T cells for cellular therapy. The technologies implemented by each module in the system can include any combination of microfluidic acoustophoresis, microfluidic (Continued)

200 acoustophoretic media exchange or cell washing, and continuous-flow microfluidic electrotransfection. Modules implementing these microfluidic technologies can be interconnected with plastic tubing or with a custom manifold.

13 Claims, 19 Drawing Sheets

(51) Int. Cl.

| | | |
|---|---|---|
| *C12M 1/00* | (2006.01) | |
| *C12M 1/26* | (2006.01) | |
| *C12M 1/36* | (2006.01) | |
| *C12N 5/078* | (2010.01) | |
| *C12N 5/0787* | (2010.01) | |

(52) U.S. Cl.
CPC ............ *C12M 29/00* (2013.01); *C12M 33/08* (2013.01); *C12M 41/48* (2013.01); *B01L 2300/0645* (2013.01); *B01L 2400/0439* (2013.01); *C12N 5/0634* (2013.01); *C12N 5/0641* (2013.01); *C12N 5/0642* (2013.01); *C12N 2521/10* (2013.01)

(56) References Cited

U.S. PATENT DOCUMENTS

| | | | | |
|---|---|---|---|---|
| 2009/0326720 | A1* | 12/2009 | Ludwig | G05D 7/0694 |
| | | | | 700/282 |
| 2010/0303687 | A1* | 12/2010 | Blaga | F16K 99/0015 |
| | | | | 156/247 |
| 2011/0089328 | A1 | 4/2011 | Li | |
| 2012/0222747 | A1* | 9/2012 | Easley | F16K 99/0057 |
| | | | | 137/340 |
| 2016/0018296 | A1* | 1/2016 | Eubisch | C12M 33/12 |
| | | | | 435/309.1 |
| 2016/0108433 | A1* | 4/2016 | Fair | C12M 35/02 |
| | | | | 435/173.6 |
| 2018/0313816 | A1 | 11/2018 | Fiering et al. | |
| 2019/0055509 | A1 | 2/2019 | Meacham et al. | |
| 2019/0119624 | A1 | 4/2019 | Tandon et al. | |
| 2019/0290829 | A1 | 9/2019 | Fiering et al. | |
| 2019/0292565 | A1 | 9/2019 | Tandon et al. | |
| 2019/0338235 | A1 | 11/2019 | Coppeta et al. | |

OTHER PUBLICATIONS

Kim "Integrated microfluidic-based sensor module for real-time measurement of temperature, conductivity, and salinity to monitor reverse osmosis" 2013. (Year: 2013).*
Andreas Lenshof et al., "Efficient Purification of CD4+ Lymphocytes from Peripheral Blood Progenitor Cell Products Using Affinity Bead Acoustophoresis", Cytometry Part A, vol. 85, No. 11, Jul. 22, 2014 (Jul. 22, 2014), pp. 933-941.
International Preliminary Report on Patentability on PCT Appl. Ser. No. PCT/US2020/061571 dated Jun. 2, 2022 (10 pages).
International Search Report and Written Opinion on PCT Appl. Ser. No. PCT/US2020/061571 dated Apr. 28, 2021 (16 pages).
Invitation to Pay Additional Fees on PCT Appl. Ser. No. PCT/US2020/061571 dated Mar. 5, 2021 (12 pages).
Office Action issued in corresponding Japanese Patent Application No. 2022-529967 dated Nov. 26, 2024.
Office Action issued in corresponding Chinese Patent Application No. 202080093953.0 dated May 24, 2025.

* cited by examiner

500

500

500

1100

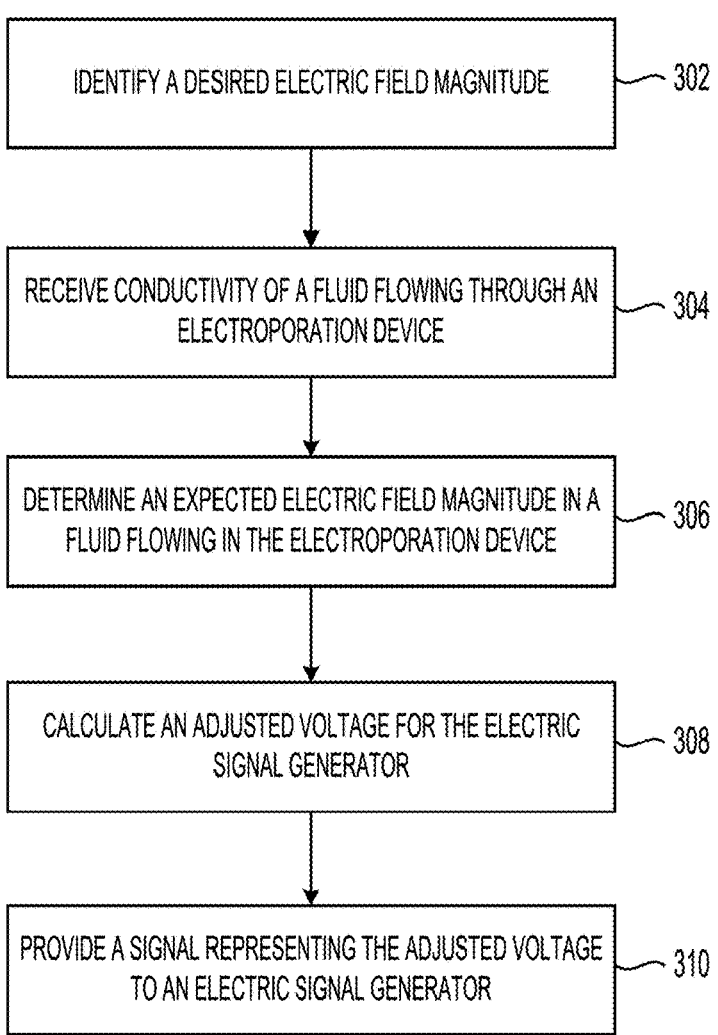

IDENTIFY A DESIRED ELECTRIC FIELD MAGNITUDE — 302

RECEIVE CONDUCTIVITY OF A FLUID FLOWING THROUGH AN ELECTROPORATION DEVICE — 304

DETERMINE AN EXPECTED ELECTRIC FIELD MAGNITUDE IN A FLUID FLOWING IN THE ELECTROPORATION DEVICE — 306

CALCULATE AN ADJUSTED VOLTAGE FOR THE ELECTRIC SIGNAL GENERATOR — 308

PROVIDE A SIGNAL REPRESENTING THE ADJUSTED VOLTAGE TO AN ELECTRIC SIGNAL GENERATOR — 310

FIG. 11

END-TO-END CELL THERAPY BIOPROCESSING DEVICE FOR CONTINUOUS-FLOW ENRICHMENT, WASHING, AND ELECTROTRANSFECTION OF TARGET CELLS

CROSS REFERENCE TO RELATED APPLICATIONS

The present application claims priority under 35 U.S.C. § 119(e) to U.S. Provisional Patent Application No. 62/939,191, titled "END-TO-END CELL THERAPY BIOPRO-CESSING DEVICE FOR CONTINUOUS-FLOW ENRICHMENT, WASHING, AND ELECTROTRANS-FECTION OF TARGET CELLS," filed Nov. 22, 2019, which is incorporated herein by reference in its entirety.

BACKGROUND

The use of genetically-modified T cells can be used to treat various hematological cancers, leading to the first FDA-approved cell therapy treatments. Successful cell therapy treatments have led to new cell therapy research and increased demand for cell therapy manufacturing. Current manufacturing pipelines often rely on antiquated cell bio-processing equipment designed for research use rather than large-scale manufacturing. This can result in long processing times (e.g., on the order of weeks) and very expensive treatments, with costs to the patients reaching approximately $400,000 per dose in some cases.

SUMMARY

The present disclosure describes systems and methods for cell bioprocessing and cell therapy manufacturing. In some implementations, the techniques of this disclosure can use a combination of microfluidics-based technologies to stream-line and automate a cell bioprocessing or manufacturing process for cellular therapies. The systems and methods of this disclosure can make use of several steps in a manufac-turing process, including enrichment of target cells from blood or blood product, cell washing or media exchange, and gene delivery via electrotransfection. In some imple-mentations, all of these processing steps can be accom-plished in continuous flow, enabling processing of on the order of 1 billion cells in a few hours in a completely automated process with no human intervention.

In some implementations, a system for cell bioprocessing and cell therapy manufacturing can be built primarily from microfluidic modules, and can enable continuous-flow end-to-end cell bioprocessing. Traditionally, microfluidic solu-tions can be limited by low throughput. However, the techniques disclosed herein can use parallelization and meso-scale geometries (e.g., 1 mm wide microchannels) to overcome these limitations to manufacture cell therapies at clinical scale. This disclosure also describes feedback sen-sors for automated precision control over critical param-eters, such as flow rates and electric field magnitude. This can help to ensure that the final product is consistent throughout processing of large samples, which may include more than 500,000 cells. Thus, this disclosure provides techniques that can offer increased automation, reduced touch labor, increased throughput, and more precise control over the processes used for cell bioprocessing and cell therapy manufacturing.

At least one aspect of the present disclosure is directed to a system. The system can include an inlet channel that receives a target fluid flow comprising target particles. The system can include an acoustophoresis device that receives the target fluid flow comprising the target particles from the inlet channel and moves the target particles from the target fluid flow to a buffer fluid flow comprising cargo particles. The system can include an electroporation device that receives the buffer fluid flow comprising the target particles and the cargo particles. The electroporation device can apply an electric field to the buffer fluid flow to cause a portion of the target particles in the buffer fluid flow to absorb a portion of the cargo particles. The system can include an outlet channel that provides an output buffer fluid flow from the electroporation device.

In some implementations, the acoustophoresis device can include a central channel that receives the buffer fluid flow comprising the cargo particles from a source of buffer fluid and the target fluid flow from the inlet channel. In some implementations, the acoustophoresis device can include a piezoelectric transducer coupled to the central channel that causes the target particles to move from the target fluid flow to the buffer fluid flow in the second channel. In some implementations, the electroporation device can include a central channel receiving the buffer fluid flow output from the acoustophoresis device and a conductive buffer flow from a second channel. In some implementations, the elec-troporation device can include an electrode electrically coupled to a portion of the central channel that provides the electric current.

In some implementations, the target particles in the input fluid flow can be lymphocytes. In some implementations, the input fluid flow further comprises waste particles including at least one of red blood cells, granulocytes, or monocytes. In some implementations, the system can include a second inlet channel that receives an input fluid flow comprising the target particles and waste particles. In some implementa-tions, an acoustic separation device that receives the input fluid flow comprising the target particles and the waste particles from the second inlet channel and separates the input fluid flow into the target fluid flow comprising the target particles and a waste fluid flow comprising the waste particles. In some implementations, the waste fluid flow can be transported via one or more channels to a waste reservoir. In some implementations, the target fluid flow output from the acoustic separation device is transported via a second channel into a target reservoir. In some implementations, the system can include a pump that transports the target fluid flow from the target reservoir to the acoustophoresis device via the inlet channel.

In some implementations, the system can include a first pump that transports the target fluid flow from an input reservoir to the acoustophoresis device via the inlet channel. In some implementations, the system can include a second pump that transports the buffer fluid flow comprising the target particles and the cargo particles output from the acoustophoresis device to the electroporation device via an intermediate channel. In some implementations, the system can include one or more holding reservoirs between two or more of the inlet channel, the acoustophoresis device, the electroporation device, or the outlet channel. In some imple-mentations, the system can include a separation device that receives the output buffer fluid flow from the output channel and separates enriched target particles in the output buffer fluid flow from waste particles in the output buffer fluid flow. In some implementations, the system can include an output reservoir that receives the enriched target particles from the separation device.

In some implementations, connections between at least the inlet channel, the acoustophoresis device, the electroporation device, or the outlet channel comprise at least one of poly-vinyl-chloride tubing or silicone tubing. In some implementations, the system can include one or more fluid capacitors coupled with at least one the connections, the fluid capacitors configured to regulate the flow rate of fluids in the system. In some implementations, the system can include one or more sensors configured to transmit, to a controller device, signals representing a density value of the target particles or waste particles in at least one of the target fluid flow, the buffer fluid flow, or the output buffer fluid flow. In some implementations, the system can include one or more flow sensors that transmit, to a controller device, signals representing a flow rate or a conductivity of fluids flowing through at least one of the inlet channel, the acoustophoresis device, the electroporation device, or the outlet channel.

At least one other aspect of the present disclosure is directed to a system. The system can include a sensor upstream of an electroporation device that measures a conductivity of a fluid flowing into the electroporation device. The system can include an electric signal generator that generates a voltage in the electroporation device. The system can include a controller device comprising one or more processors coupled to memory. The controller device can identify a desired electric field magnitude to induce in the fluid flowing through the electroporation device. The controller device can receive, from the sensor, the conductivity of the fluid flowing into the electroporation device. The controller device can determine an expected electric field magnitude in the fluid as the fluid flows through the electroporation device based on the conductivity and the voltage generated by the electric signal generator. The controller can calculate an adjusted voltage for the electric signal generator based on the expected electric field magnitude and the desired electric field magnitude. The controller can provide a signal representing the adjusted voltage to the electrical signal generator, causing the electric signal generator to generate a second voltage in the electroporation device.

In some implementations, the system can include a conductivity probe that measures a second conductivity of the fluid as the fluid flows through the electroporation device. In some implementations, the system can include a current sensor that measures an electric current passing through the fluid as the fluid flows through the electroporation device. In some implementations, the system can include an optical sensor that measures a width of a center portion of the fluid as the fluid through the electroporation device. In some implementations, the controller device can determine the expected electric field magnitude based on the second conductivity, the electric current, and the width of the center portion of the fluid.

In some implementations, the fluid flowing through the electroporation device includes a first fluid from a first fluid input and a second fluid from a second fluid input. In some implementations, the controller device can calculate an adjusted flow rate for at least one of the first fluid or the second fluid based on the second conductivity, the electric current, and the width of the center portion of the fluid. In some implementations, the controller device can provide a second signal representing the adjusted flow rate to a pump that controls the flow of the first fluid or the second fluid, causing the first fluid or the second fluid to flow at a second flow rate.

In some implementations, the fluid flowing through the electroporation device can include a first fluid from a first fluid input and a second fluid from a second fluid input. In some implementations, the electroporation device can include a second sensor that determines a first flow rate of the first fluid at the input of the electroporation device and a second flow rate of the second fluid at the input of the electroporation device. In some implementations, the controller device can calculate an adjusted flow rate for at least one of the first fluid or the second fluid based on at least one of the first flow rate or the second flow rate. In some implementations, the controller device can provide a second signal representing the adjusted flow rate to a pump that controls the first flow rate of the first fluid or second flow rate of the second fluid, causing the first fluid or the second fluid to flow at a third flow rate.

Yet another aspect of the present disclosure is directed to a method. The method can be performed by a controller device having one or more processors and memory. The method can include identifying a desired electric field magnitude to induce in a fluid flowing through an electroporation device. The method can include receiving, from a first sensor, a conductivity of the fluid as the fluid flows into the electroporation device. The method can include determining an expected electric field magnitude in the fluid as the fluid flows through the electroporation device based on the conductivity and a voltage generated by an electric signal generator. The method can include calculating an adjusted voltage for the electric signal generator based on the expected electric field magnitude and the desired electric field magnitude. The method can include providing a signal representing the adjusted voltage to the electric signal generator, causing the electric signal generator to generate a second voltage in the electroporation device.

In some implementations, the method can include receiving, from one or more second sensors detecting signals from the fluid in the electroporation device, a second conductivity of the fluid, an electric current passing through the fluid, and a width of a center portion of the fluid. In some implementations, the method can include determining the expected electric field magnitude based on the second conductivity, the electric current, and the width of the center portion of the fluid. In some implementations, the fluid flowing into the electroporation device is received from a first fluid flow and a second fluid flow. In some implementations, the method can include receiving, from at least one flow rate sensor, a first fluid flow rate of the first fluid flow and a second fluid flow rate of the second fluid flow. In some implementations, the method can include calculating an adjusted flow rate for at least one of the first fluid flow or the second fluid flow. In some implementations, the method can include providing a signal representing the adjusted flow rate to a pump that controls the first fluid flow or the second fluid flow, causing the first fluid flow or the second fluid flow to flow at a second flow rate.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification. Aspects can be combined and it will be readily appreciated that features described in the context of one aspect of the invention can be combined with other aspects. Aspects can be implemented in any convenient form.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. The foregoing and other objects, aspects, features, and advantages of the disclosure will become more apparent and better understood by referring to the following description taken in conjunction with the accompanying drawings, in which:

FIG. 11 illustrates a flow diagram of an example method of controlling a flow rate or an electric field experienced by fluids flowing in a system similar to that depicted in FIGS. 5A, 5B, and 5C.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The present disclosure describes systems and methods for cell bioprocessing and cell therapy manufacturing. In some implementations, the techniques of this disclosure can use a combination of microfluidics-based technologies to streamline and automate the manufacturing process for cellular therapies. The systems and methods of this disclosure can make use of several steps in the cell bioprocessing or cell therapy manufacturing process, including enrichment of target cells from blood or blood product, cell washing or media exchange, and gene delivery via electrotransfection. In some implementations, all of these processing steps can be accomplished in continuous flow, enabling processing of on the order of 1 billion cells in a few hours in a completely automated process with no human intervention.

In some implementations, a system for cell bioprocessing and cell therapy manufacturing can be built primarily from microfluidic modules, and can enable continuous-flow end-to-end cell bioprocessing. For example, a series of modules each implementing a different technology can be coupled to one another to perform various unit operations in the cell-therapy manufacturing chain to enable direct processing of a blood or blood product sample. In some implementations, the sample can be a leukopak obtained from leukapheresis. The system can automatically and continuously process the sample into genetically-modified lymphocytes or T cells for cellular therapy. In some implementations, the technologies implemented by each module in the system can include any combination of microfluidic acoustophoresis, microfluidic acoustophoretic media exchange or cell washing, and continuous-flow microfluidic electrotransfection. Modules implementing these microfluidic technologies can be interconnected with plastic tubing (e.g., silicone or vinyl tubing) or a custom-built manifold as part of an integrated, automated system.

Figure 1:
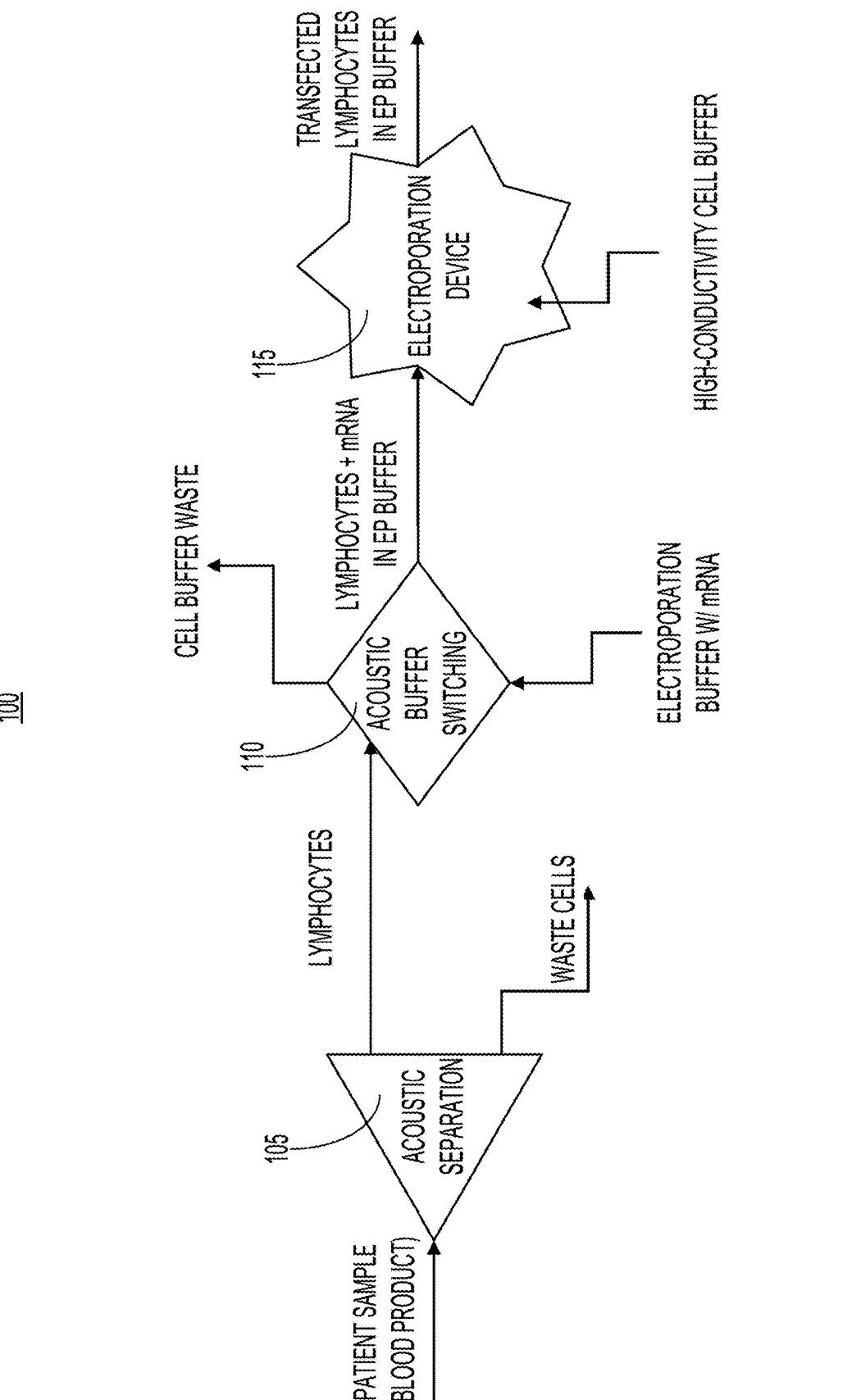
FIG. 1 illustrates an example process flow diagram for a method of cell therapy manufacturing, in accordance with one or more implementations.

FIG. 1 illustrates an example process flow diagram for a method 100 of cell therapy manufacturing. The process flow diagram 100 includes three stages. In a first stage 105, a blood sample can be acoustophoretically enriched for lymphocytes (or other types of cells, such as T cells, in other implementations). For example, blood product can be introduced into a module configured to enrich the sample for lymphocytes using acoustic separation. Waste cells can be discarded, and the enriched sample can be introduced into a second stage 110. The second stage 110 can be implemented, for example, using a media exchange device. In the second stage 110, the target cells can be acoustophoretically transferred into electroporation media in a media-exchange module. Acoustophoresis can be used to move the cells into a low-conductivity electroporation buffer that contains cargo, which may include nucleic acids, proteins, or a combination of these materials in the second stage 1100. In some implementations, the cargo can include mRNA. Then, the media containing the target cells can be delivered to a third stage 115. In some implementations, the third stage 115 can be implemented using an electroporation device. In the third stage 115, the cells can be electroporated in the continuous-flow electroporation device.

The arrangement of the stages 105, 110, and 115 shown in FIG. 1 is illustrative only. In some other implementations, the modules that implement the first stage 105, the second stage 110, and the third stage 115 may be configured in various sequences or permutations, or configured in various series and parallel networks and interconnected to automate a desired workflow. For example, in some implementations acoustic enrichment for target cells can be performed in the last stage, after media exchange and electroporation are performed in earlier stages. In addition to the stages shown in FIG. 1, this disclosure provides infrastructure for maintaining continuous flow from one stage to the next, holding reservoirs with agitation to maintain cells in suspension at the front end of the device and between processing steps, a controller, sensors and feedback control, and pumps, all of which are described further below. In some implementations, the entire system can be closed to maintain sterility.

Figure 2:
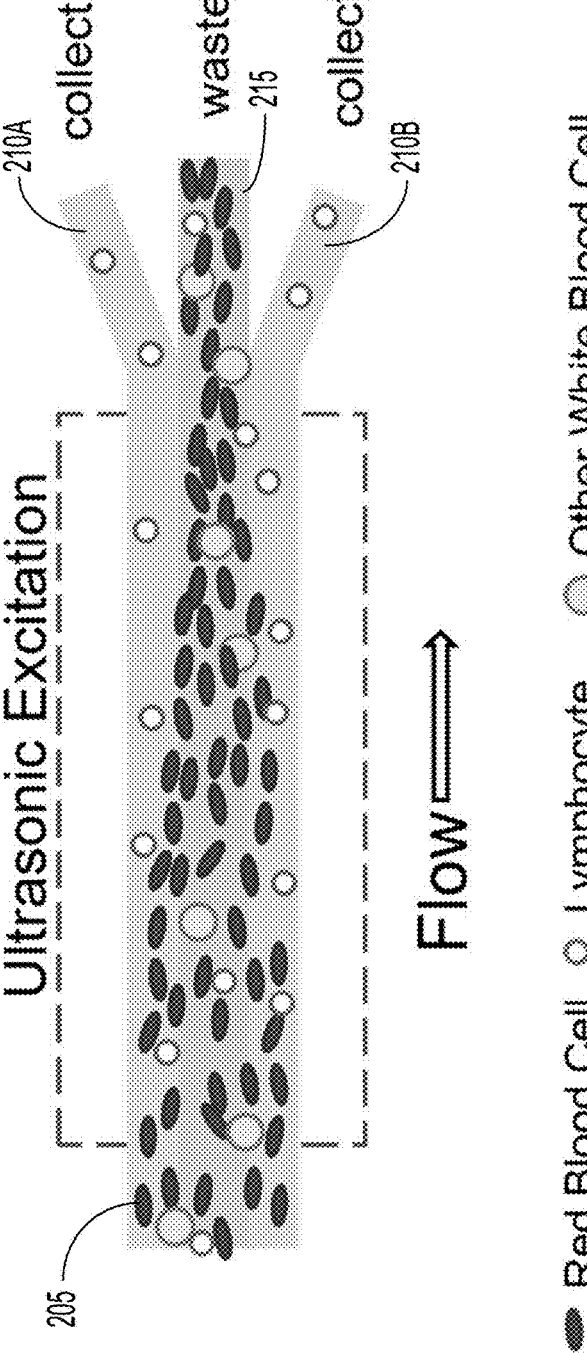
FIG. 2 illustrates an example module that can be used to implement the first stage of the process flow of FIG. 1, in accordance with one or more implementations.

FIG. 2 illustrates an example module 200 that can be used to implement the first stage 105 of the process flow 100 of FIG. 1. In the module 200, acoustophoresis can be used to enrich lymphocytes and deplete erythrocytes from a sample that includes blood or blood product. The module 200 includes a set of microchannels having an inlet 205 and three outlets 210a, 210b, and 215. In some implementations, a wall of the inlet channel 205 can be coupled to an ultrasonic oscillator such as a piezoelectric transducer, and the transducer can be electrically driven to excite the inlet channel 205 such that some cells migrate toward the axial center stream of the channel as they flow through it. The migration rate of the cells can depend on their size, density, and compressibility relative to the surrounding media, and therefore differences in the inherent properties of the cells can be such that some cell types will migrate more rapidly than others and can be collected in the center outlet 215 while the remaining cells will be collected in side outlets 210a and 210b. In the example of FIG. 2, red blood cells, granulocytes, and monocytes can be enriched in the center outlet 215 and lymphocytes can be enriched in the side outlets 210a and 210b. The cells and media that flow to the center outlet 215 can be waste products, which may be discarded. The cells and media that flow to the side outlets 210a and 210b can be collected and introduced into a subsequent stage of the system (e.g., stage 110 of FIG. 1). In some implementations, modifications to the media, the addition of particles, or inducing the cells into other states/phenotypes or aggregates can further aid the separation process in the module 200.

Figure 3:
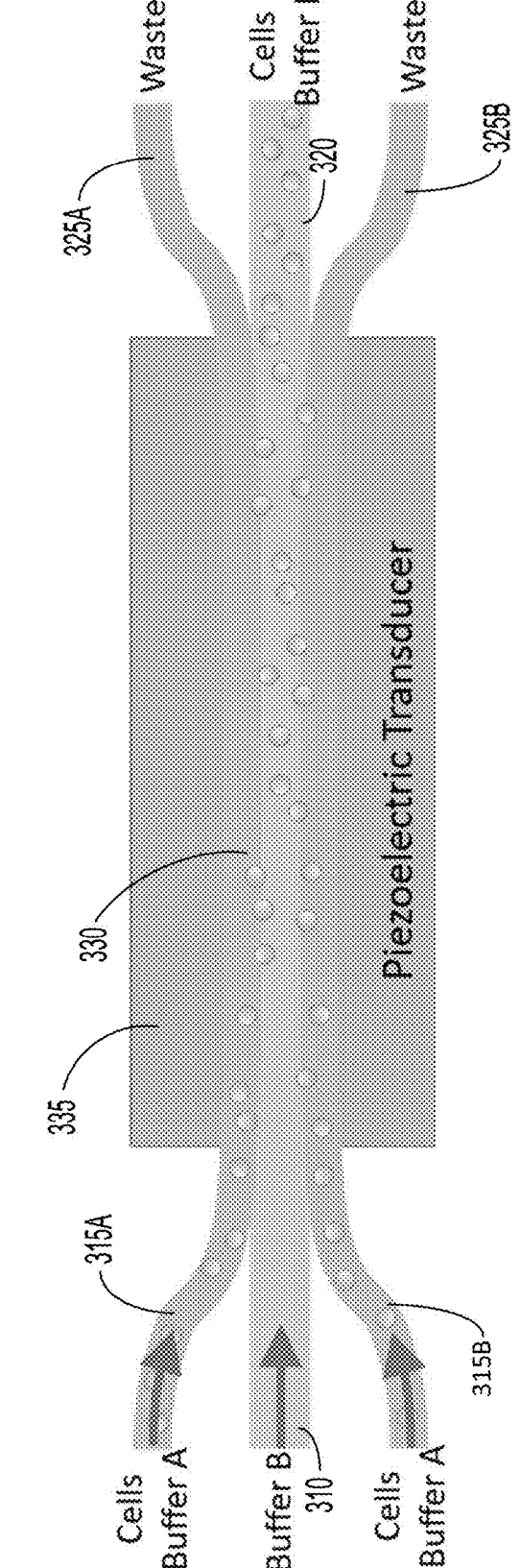
FIG. 3 illustrates an example module that can be used to implement the second stage of the process flow of FIG. 1, in accordance with one or more implementations.

FIG. 3 illustrates an example module 300 that can be used to implement the second stage of the process flow of FIG. 1. In the module 300, acoustophoresis can be used to move cells from one media into another. In particular, the module 300 can move target cells from an initial medium (e.g., blood plasma or cell culture medium) into an electroporation medium that is compatible with an upstream microfluidic electroporation module. The module 300 can include three inlets, including a center inlet 310 and two side inlets 315a and 315b. The module 300 can include three outlets, including a center outlet 320 and two side outlets 325a and 325b. A central channel 330 can couple the three inlets with the three outlets. A piezoelectric transducer 335 can be coupled with the central channel 330.

In the module 300, three parallel streams can be established in a laminar flow regime, with each stream corresponding to one of the two side inlets 315a or 315b or the center inlet 310. Mixing between the streams in the central channel 330 can be dominated by diffusion and dispersion. An acoustic radiation field generated by the piezoelectric transducer 335 can be used to manipulate particles with respect to the streams in the central channel 330, and can therefore be used to move the particles from one stream to another. The central channel 330 can be a microchannel fabricated from a hard substrate, such as silicon, glass or quartz, or a polymer with high acoustic impedance, such as polystyrene. The central channel 330 can be rectangular in cross section, with width and height dimensions that can range from 100 μm to 1000 μm. The length of the central channel can range from 5 mm to 200 mm. In the configuration shown in FIG. 3, the center fluid stream can have a density that is equal to or greater than the density of the side streams. In some implementations, the density of the center stream can be adjusted using additives to achieve the needed density contrast.

Under the influence of the acoustic radiation field generated by the piezoelectric transducer 335, the media can remain primarily in their respective streams, while the cells introduced in the side outlets 315a and 315b migrate into the center stream. The center stream with the cells can be collected from the center outlet 320. The media flowing to the side outlets 325a and 325b can be discarded as waste. Thus, the cells of interest are moved out of their initial media and into the media introduced via the center inlet 310, which can be collected for introduction into a subsequent stage (e.g., the third stage 115 of FIG. 1).

Figure 4:
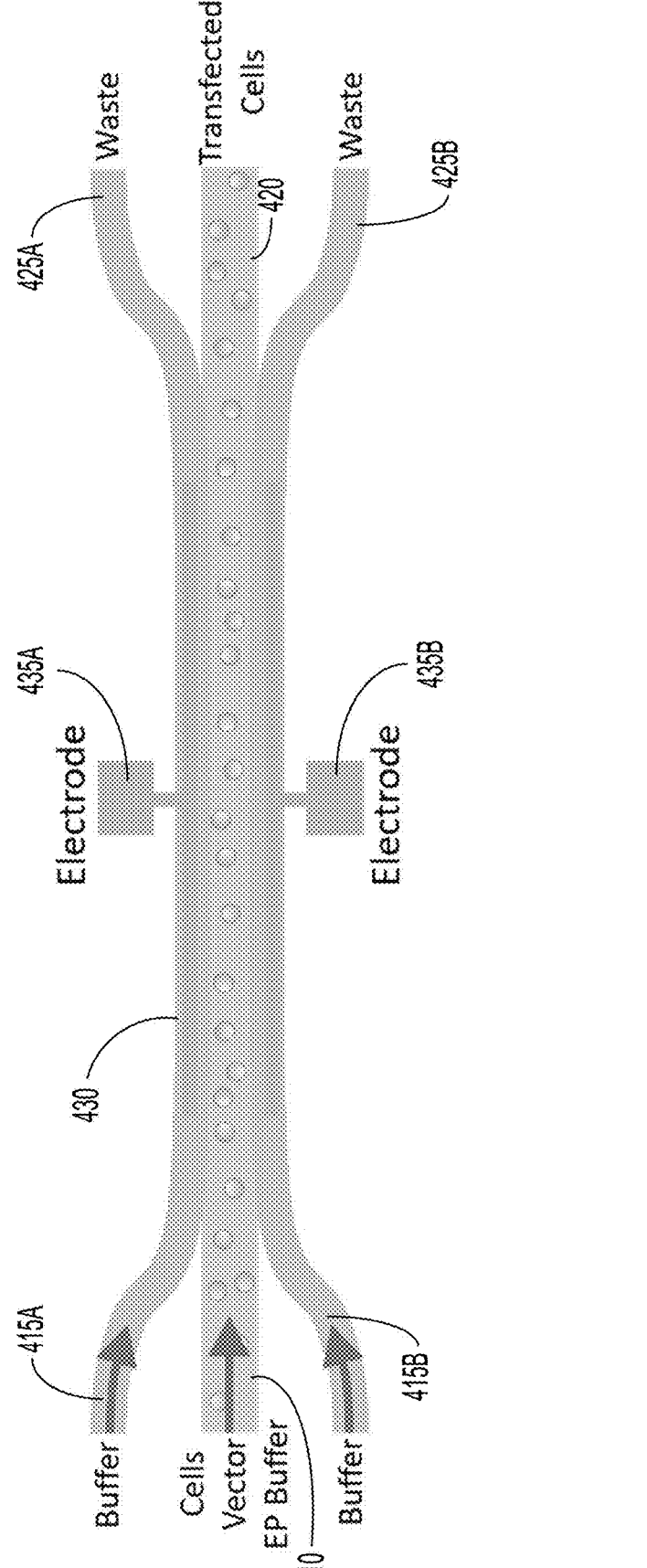
FIG. 4 illustrates an example module that can be used to implement the third stage of the process flow of FIG. 1, in accordance with one or more implementations.

FIG. 4 illustrates an example module 400 that can be used to implement the third stage of the process flow of FIG. 1. In the module 400, cells can be electroporated in continuous flow. The module 400 can include three inlets, including a center inlet 410 and two side inlets 415a and 415b. The module 400 can include three outlets, including a center outlet 420 and two side outlets 425a and 425b. A central channel 430 can couple the three inlets with the three outlets. A pair of electrodes 435a and 435b can be coupled with the central channel 430. In some implementations, cells and cargo can be introduced in the center stream in low-conductivity media via the center inlet 410. High conductivity media streams that are in contact with stimulation electrodes 435a and 435b can be introduced via the side inlets 415a and 415b, and can flank the central stream. This configuration can keep cells away from direct contact with electrodes 435a and 435b while exposing them to high-magnitude electric fields.

In some implementations, the module 400 can apply pulsed electric fields to the target cells in continuous flow to temporarily permeabilize them, rendering them susceptible to uptake of the cargo and genetic manipulation. In some implementations, the central channel 430 can be a microchannel fabricated from a hard plastic (e.g., cyclic olefin copolymers, Kapton, polystyrene, Ultem, etc.) and can support a sheath flow or co-flow configuration with three parallel, laminar streams. In some implementations, the channel dimensions in the module 400 can range from 500 μm to 3 mm in width, 1 cm to 5 cm in length, and 125 μm to 500 μm in height.

The electrodes 435a and 435b can be coplanar rectangular electrodes that are patterned onto the floor of the central channel 430. The electrodes 435a and 435b can have dimensions of 100 μm to 250 μm in width and 8 μm to 45 mm in length. In some implementations, the electrodes 435a and 435b can interface with a power source via a connection to soldering pads. In some implementations, the electrodes 435a and 435b can be positioned between 50 μm and 300 μm away from the walls of the central channel 430. The electrodes 435a and 435b can be formed from an electrochemically stable material, such as platinum.

The center fluidic stream in the central channel 430 can contain cells and cargo suspended in low-conductivity electroporation buffer (e.g., 0.01-0.1 S/m), which can be introduced via the center inlet 410. The side streams in the central channel 430 can include a high-conductivity cell culture buffer (e.g., 1-2 S/m). A relevant parameter for electroporation can be the ratio of the side stream conductivity to the center stream conductivity. In some implementations, that ratio can be 20 or greater. For example, the center stream conductivity can be in the range of 1-2 S/m when the side stream conductivity is in the range of 20-40 S/m. The relative flow rates of the center stream compared to the side streams in the central channel 430 can be tuned such that the electrodes 435a and 435b only make contact with the side streams. In this configuration, the center stream can dominate the electrical resistance of the circuit, such that when voltage is applied to the electrodes 435$a$ and 435$b$, most of the voltage is dropped across the center stream. In some implementations, the applied voltage can take the form of a sinusoid with a period ranging from 10 ns to 10 ms. In some implementations, the applied voltage can take the form of a pulse train with pulse widths ranging from 10 ns to 10 ms. In some implementations, the magnitude of the applied voltage can vary so as to generate an electric field across the center stream that ranges from about 2-600 kV/m, with pulse widths ranging from 10 ns to 10 ms. The sample containing the transfected cells can be collected via the center outlet 420, while media from the side outlets 425$a$ and 425$b$ can be treated as waste product and discarded.

Figure 5A:
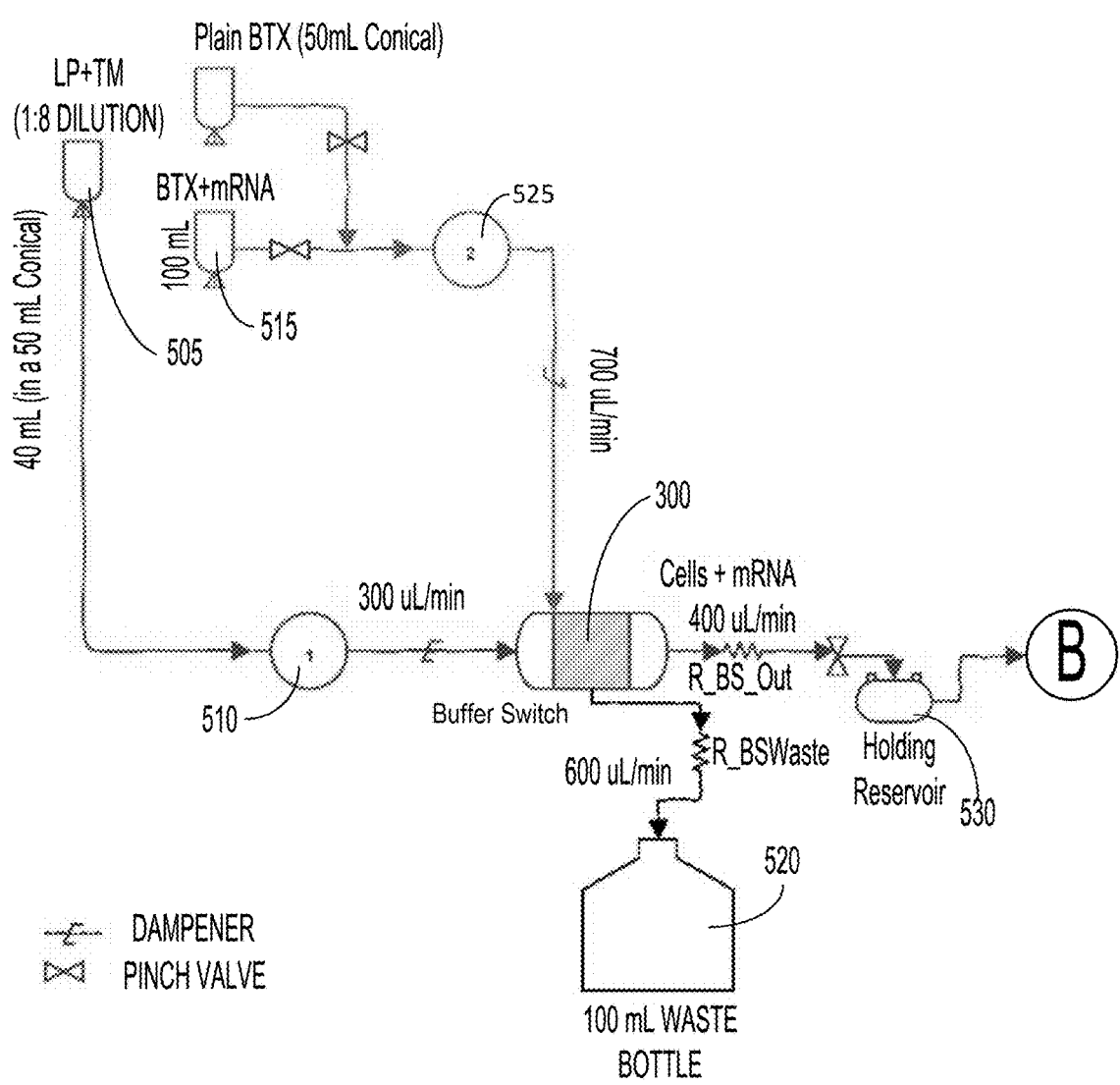
FIGS. 5A, 5B, and 5C illustrate a block diagram of a system for implementing a process flow similar to that shown in FIG. 1, in accordance with one or more implementations.
Figure 5B:
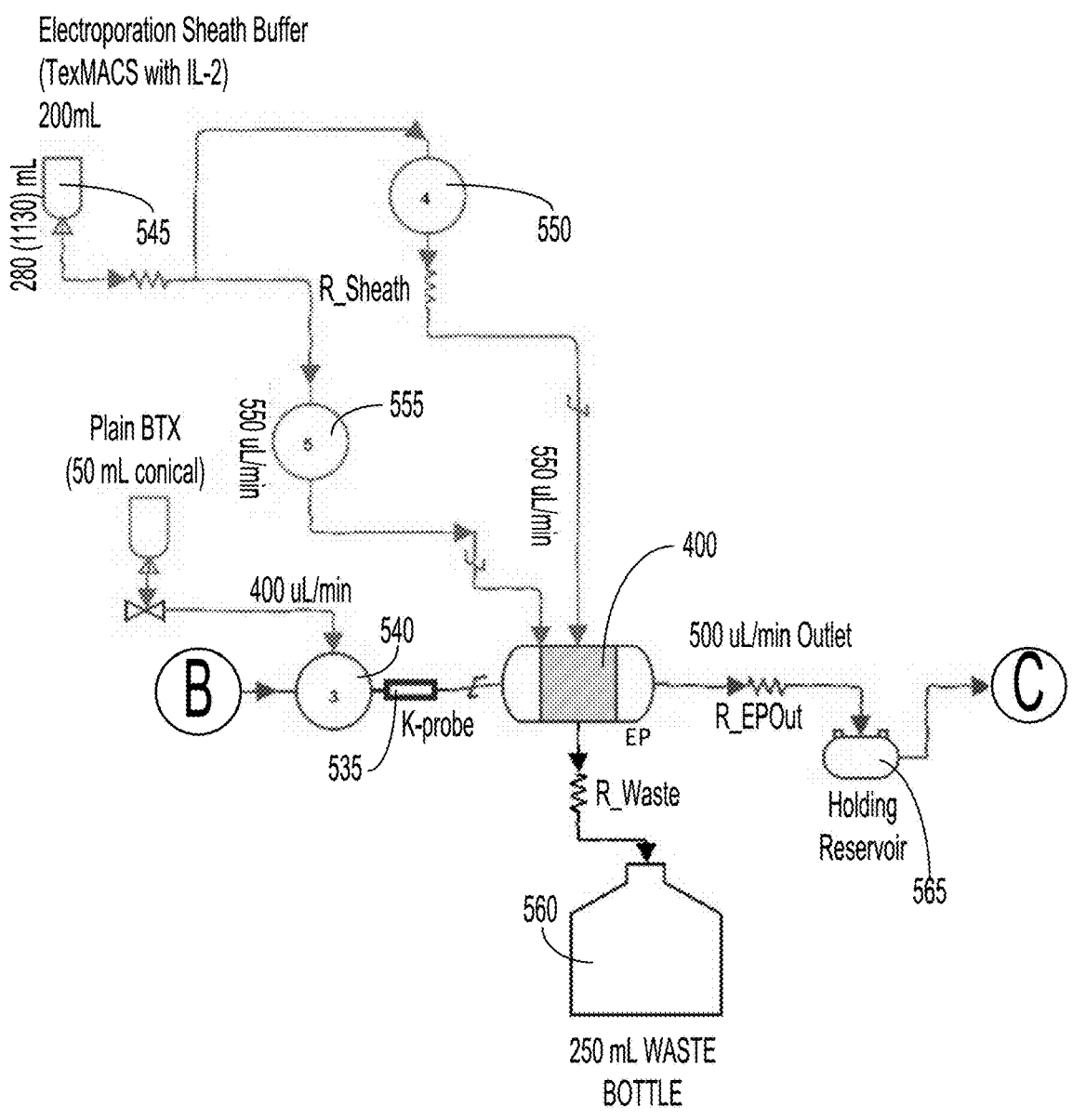
Figure 5C:
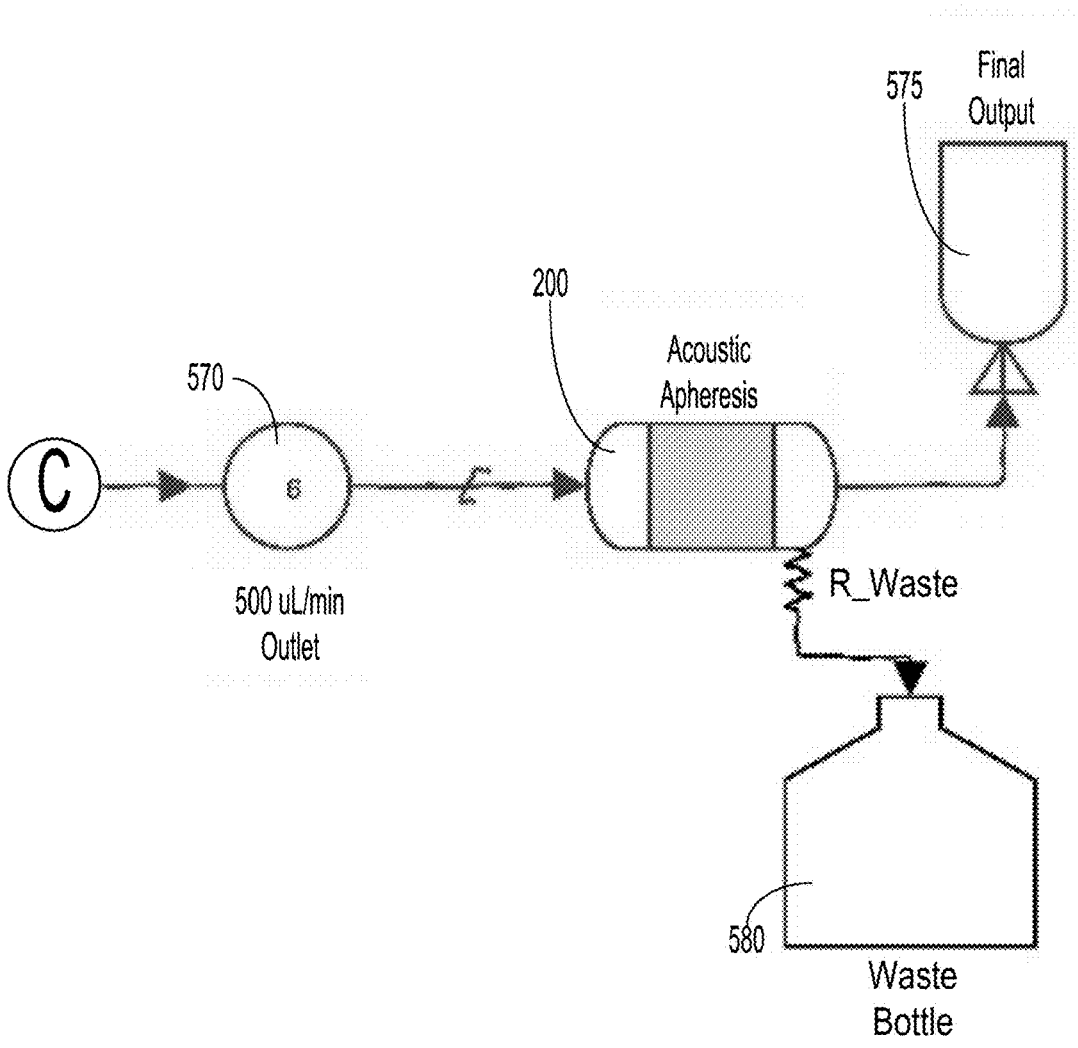

In some implementations, the microfluidic modules or devices (e.g., the module 200, the module 300, the module 400, etc.) described herein can be interconnected with one another to form a process flow, similar to the process flow system 500 described herein in conjunction with FIGS. 5A, 5B, and 5C. The microfluidic modules described herein can be disposed within a layer or a substrate. For example, each of the microfluidic devices or channels can be disposed within a single substrate sheet, which can form a layer. In some implementations, different substrates can be used for one or more of the microfluidic modules or devices described herein, and each of the substrates can be connected via tubing, other microfluidic substrate channels, or other fluid connection means. In addition, microfluidic valves can be embedded in one or more microfluidic substrates forming the layers, along with any of the other microfluidic components or features described herein (e.g., pumps, sensors, reservoirs, waste bottles, pinch valves, etc.) to control the flow of fluids as they flow through the microfluidic channels, similar to the components described in conjunction with the system 500.

In some implementations, the microfluidic devices can form a portion of a layer of a process flow, which can be scaled by multiplexing microfluidic channels across multiple, parallel layers. Each layer in the process flow can include one or more of the microfluidic modules or devices (e.g. the module 200, the module 300, the module 400, etc.), microfluidic channels to transport fluid between microfluidic modules or devices, and other microfluidic devices (e.g., fluid capacitors, fluid reservoirs, valves, pumps, any other microfluidic features described herein, etc.). It will be appreciated that any layer of microfluidic devices can include any number of ports (e.g., inlet ports, outlet ports, etc.), at any stage in the process flow to introduce or remove fluid from a particular layer. Ports can include one or more connectors (e.g., threaded connectors, snap connectors, friction-fit connectors, press-fit connectors, etc.) that can be coupled to other fluid lines, such as those from one or more reservoirs. Thus, in implementations having multiple layers of microfluidic devices or features, fluid from a fluid source can be provided to multiple layers by multiplexing a fluid line from that fluid source to inlet ports of each layer.

In some implementations, ports from one layer can be connected to ports of another layer, allowing fluid to flow between each layer. Multiple layers can be used to form a stack of microfluidic layers and devices. In some implementations, the microfluidic layer stack can have similar components to the other layers in the microfluidic stack, allowing a process flow defined by the microfluidic devices (e.g., the module 200, the module 300, the module 400, etc.) to be defined in parallel networks of microfluidic devices. The parallel layers can define parallel microfluidic portions of a microfluidic path (e.g., the microfluidic paths or channels described herein below in conjunction with FIGS. 5A, 5B, and 5C, etc.), either in a lateral layer design or by adding vertical layers of microchannel networks for steps such as cell separation or transduction. Said another way, the process flow systems, or microfluidic components, can be expanded or scaled using one or more layers of microfluidic devices, which can be arranged in a lateral (e.g., sequential, etc.) arrangement or a parallel arrangement, or any combination thereof.

FIGS. 5A, 5B, and 5C illustrate portions of a block diagram of a system 500 for implementing a process flow similar to the process flow 100 shown in FIG. 1. The system 500 shows the components required for connection and support, in addition to the microfluidic devices. In some implementations, at least some of the microfluidic devices shown in FIGS. 5A, 5B, and 5C can correspond to the modules of FIGS. 2-4, which can be used to implement the stages of the process flow 100 of FIG. 1. Microfluidic devices, such as instances of the modules 200, 300, and 400 of FIGS. 2-4, respectively, as well as valves, sensors, and holding reservoirs, are shown. A legend is included in FIG. 5A that indicates symbols used for dampeners and pinch valves in the system 500, as shown in FIGS. 5A, 5B, and 5C. Circles can represent peristaltic pumps that can drive fluid through the system 500 and can help to maintain correct flow rates.

Referring now to FIG. 5A, at the front end of the system 500, a user can deposit the target cells in culture media into a holding reservoir 505. The reservoir 505 can have an agitation mechanism to keep the cells in suspension, such as a magnetically-driven impeller. In some implementations, the agitation mechanism can be configured to agitate the media in a manner that is gentle enough not to damage the cells. The reservoir 500 at the front end of the system 500 can be connected via tubing to the center inlet of an acoustophoretic rapid media exchange device, which is depicted as the module 300 in FIG. 5A. The module 300 of FIG. 5A can be an instance of the module 300 shown in FIG. 3. A peristaltic pump 510 can deform the tubing to actuate flow through the module 300. Another reservoir 515 that contains the cargo to be transfected (e.g., mRNA) suspended or dissolved in an electroporation buffer can be connected to the side inlets of the module 300. Waste product from the module 300 can be collected in the reservoir 520. Another peristaltic pump 525 can drive flow from the reservoir 515 into the side stream inlets of the module 300. As described above, an acoustic field in the module 300 can drive cells from the side streams into the center stream, and they can exit from the center outlet, suspended in electroporation media with cargo. At the outlet of the module 300, the side streams can be collected into a reservoir 520 as waste. The center outlet of the rapid media exchange module 300 can be connected by tubing to the inlet of a holding reservoir 530, which can have an agitation mechanism to keep cells in suspension.

Referring now to FIG. 5B, the outlet of the holding reservoir 530 depicted in FIG. 5A can be connected by tubing to a flow-through conductivity measurement sensor 535, which can be connected to the center inlet of a flow electroporation device, which is represented in FIG. 5B as the module 400. The module 400 of FIG. 5B can be an instance of the module 400 shown in FIG. 4. A peristaltic pump 540 can drive flow of the cell suspension from the outlet of the holding reservoir 530, through the conductivity probe 535, and through the center stream of the electroporation module 400. Another external reservoir 545, which contains high-conductivity cell culture media (e.g., TexMACS), is connected via tubing to the side inlets of the module 400. Flow through each of the side inlets is driven by another pair of peristaltic pumps 550 and 555. As cells pass through the module 400, voltage pulses are applied to transfect them. The fluid emerging from the side outlets of the module 400 can be collected into a reservoir 560 as waste. The fluid emerging from the center outlet of the module 400, laden with transfected cells, can flow into another holding reservoir 565, which can have an agitation mechanism to help maintain cells in suspension.

Referring now to FIG. 5C, the cell suspension from the holding reservoir 565 depicted in FIG. 5B can be driven into the single inlet of a microfluidic acoustic apheresis module represented in FIG. 5C as the module 200 by a final peristaltic pump 570 acting on the tubing connecting the reservoir 565 and the module 200. The module 200 of FIG. 5C can be an instance of the module 200 shown in FIG. 2. Acoustic actuation applied to the module 200 can enrich the cell suspension for lymphocytes at the outlet of the module 200. Sample at the outlet of the module 200 is collected as the final product (e.g., transfected lymphocytes) in a reservoir 575. Fluid from the waste outlet of this module 200 can be collected in a final waste reservoir 580. Each of the modules (e.g., the modules 200, 300, and 400, etc.), the pumps (e.g., the pumps 510, 525, 540, 550, 555, 570, etc.) can be controlled via one or more signals received from the controller 1005, as described herein.

In some implementations, connections between components of the system 500 can be made using various types of polymer tubing, including, for example, 0.44" inner diameter PVC tubing that can be fed through the peristaltic pumps, ⅛" and ⅙" inner diameter Tygon tubing that can be used between components, and smaller (e.g., 0.011"-0.025" inner diameter) silicone tubing for interfacing with the modules 200, 300, and 400. Adapters can also be used to transition between tubing of different sizes as needed.

In some implementations, as described above, flow throughout the system 500 can be driven by a series of fluid pumps. In some implementations, these pumps can be peristaltic pumps. Because the flow in the peristaltic pumps is inherently pulsatile, compliant fluidic capacitors can also be introduced after each pump to smooth out fluctuations in flow rate, as steady flow may be needed for the modules 200, 300, and 400 to function correctly. Nominal flow rates generated by these pumps are shown in FIGS. 5A, 5B, and 5C for illustrative purposes, however it should be understood that these flow rates may vary in other implementations, and that these flow rates may vary as the system 500 operates. In some implementations, the pumps can move fluid and samples from reservoirs into the system 500. Thus, valves can be used to switch between input lines used for priming and setting up the system 500, and other lines used for running sample through the system 500. In some implementations, flow sensors can be placed at various locations in the fluid path (e.g., at the inlets and outlets of the modules 200, 300, and 400) and can be used for feedback control of the pumps (e.g., by the controller 1005 described herein in conjunction with FIG. 10, etc.).

As shown in FIGS. 5A, 5B, and 5C, there can be holding reservoirs between each of the modules 200, 300, and 400. These reservoirs can provide ballast to make the system 500 robust against unanticipated flow rate differentials between the output of one module and the input of the next module. In some implementations, an agitation mechanism such as a magnetically driven impeller can be used to maintain cells in suspension and prevent settling in these holding reservoirs. In order to maintain the system 500 at a consistent temperature while the various components generate heat (e.g., the acoustophoresis-based components), in some implementations either a shared heat sink or individual heat sinks for each of the modules 200, 300, and 400 can be used. Such heatsinks can also be combined with a closed-loop thermoelectric cooling system.

In some implementations, sensors can be integrated into the system 500 to enable interrogating the system 500 for operation faults and feedback or feed-forward control mechanisms. For example, sensors can be integrated either as system-wide components, or directly into the modules 200, 300, and 400. Possible sensors that can be integrated into the system 500 include flow sensors for controlling flow rates, conductivity probes, visual measurement of stream widths in sheath flows, and electrical current measurements. In some implementations, optical sensors can also be used to assess the quality of sheath flows used in the system 500, which in turn can be used to adjust flow rates as needed to generate the correct, stable flows. In some implementations, optical sensors can also be used to calibrate and tune the acoustophoretic modules, in which the optimal driving frequency for the piezoelectric components can be determined automatically by observing the concentration of cells in one of the outlet fractions.

Absorbance or impedance sensors can also be incorporated into the system 500 for real time estimates of either or both of cell concentration or cell density. This can provide information on processing throughput in the system 500, and can help to determine where there may be losses in the system 500 if cell recovery is low. Information from measurements of cell concentration can be used in closed loop control to adjust flow rates in the inlets or outlets of the modules 200, 300, and 400, to adjust acoustic power or frequency, or to adjust automated addition of reagents in the system 500.

In some implementations, sensors can be added to any of the modules 200, 300, and 400, or to locations in the system 500 between these modules, to indicate operational quality or efficiency of the functions performed by these modules. For example, sensors can be added to the module 200, or at a point in the system downstream from the module 200, to indicate or detect an efficiency of the acoustophoretic separation of cells that occurs in the module 200. Such sensors can be configured to identify cells within the fluid during or subsequent to the fluid passing through the module 200. In some implementations, sensors can be added to the module 400, or at a point downstream from the module 400, to indicate an efficiency of the transfection that occurs as a result of the operation of the module 400. Such a sensor can determine how much cargo has been introduced into the cells of the fluid sample via the electrotransfection operation performed by the module 400. In some implementations, sensors can be included in the system 500 to monitor cell viability.

Any of these sensors may provide real-time outputs, which may also be coupled with a control system, such as the controller 1005, to serve as a feedback or feed forward control mechanism. For example, based on the outputs of such sensors, adjustable parameters of any of the modules 200, 300, and 400 (e.g., fluid flow rates, fluid sample ratios, applied voltages or electric fields, etc.) can be controlled. Thus, real-time information relating to electrotransfection efficiency, separation efficiency, or cell viability can be incorporated into control data to alter the operational characteristics of the system 500 during cell processing.

In some implementations, control of the individual components of the system 500, such as the modules 200, 300, and 400, as well as design parameters of the individual components, can be selected based on characteristics of the system 500 as a whole. For example, parameters of the components of the system can be selected in an interdependent fashion, rather than independently for each individual component. Thus, some components may be designed or controlled to operate at a capacity (e.g., flow rate) that is less than the maximally achievable capacity for that component in order to improve the capacity of the system 500 as a whole. In some implementations, design parameters that may be selected in this manner can include features that may not be adjustable after the system 500 is fabricated, such as dimensional features (e.g., channel heights, channel widths, channel cross-sectional areas, channel cross-sectional shapes, etc.). Such parameters can be selected according to a routine or algorithm that improves the operation of the system 500 globally, even if the parameter selections result in sub-optimal or reduced operational capacity of one or more of the components of the system 500 individually.

It should also be understood that adjustable parameters for each component can also be selected or controlled in the same manner. For adjustable parameters, selection of suitable values may be varied over time, even during operation of the system 500. The adjustable parameters can be selected in a manner that may result in reduced throughput of one component in order to achieve increased performance (e.g., increased total throughout, increased cell viability, increased cell separation efficiency, etc.) of the system 500 as a whole. In one example, parameters for an electroporation component such as the module 400, can be selected to reduce a throughput of that component, in order to improve performance in another component (e.g., the module 200 used for cell separation) or of the system 500 globally. In some implementations, such adjustable parameters, along with fixed or non-adjustable design parameters, can be selected using a routine or algorithm that can incorporate machine learning in order to improve the operation of the system 500 on a global scale, rather than by selecting parameters for each component of the system 500 independently of one another.

As described herein, each of the components, channels, or stages of the process flow system 500 depicted in FIGS. 5A, 5B, and 5C can be established on one or more layers of microfluidic devices. For example, the layers can be arranged in a parallel fashion, which each of the microfluidic devices (e.g., the module 200, the module 300, the module 400, etc.) replicated across parallel microfluidic layers, and fed input fluid streams by multiplexing the fluid flows (e.g., using valves, junctions, or other fluid connections, etc.) across one or more of the layers in parallel. In some implementations, microfluidic channels can be multiplexed between different components (e.g., the modules 200, 300, and 400, any other microfluidic features or components described herein, etc.) on a single layer. The pumps described herein above in conjunction with FIGS. 5A, 5B, and 5C can be utilized to drive fluid flows through one or more of the parallel layers or one or more lateral layers. In some implementations, each of the microfluidic layers can have its own corresponding pump that drives fluid flow based on the conditions of that particular layer (e.g., provided by sensors to a controller such as the controller 1005, etc.).

It will be appreciated that sensors, such as the sensors described herein above disposed within the system 500 of FIGS. 5A, 5B, and 5C, can be incorporated into each of the microfluidic layers. Said another way, some or all of the process flow system 500 described herein above can be embedded in or formed as a part of a single microfluidic layer. By replicating said layers in parallel or laterally, the process flow 500 can be scaled without impacting system throughput. Signals provided to and from a controller device (e.g., the controller 1005 described herein below in conjunction with FIG. 10, etc.) can be used to manipulate and monitor the flow of fluid in each layer independently. Thus, the functionality of the controller 1005 can be used to monitor and control scaled processing of the process flow system 500 described herein.

A multi-layer process flow configuration has a number of significant advantages. One advantage of microfluidic, continuous flow systems (e.g., the system 500 described herein, etc.) in terms of reduced process time and increased safety derives from the fact that intermediate product can be moved to the next operation immediately upon completion of a process step, in a continuous fashion. This capability can reduce process cycle time and increases safety by avoiding cell damage from repeated unnecessary exposure to high cell forces. Thus, continuous flow processes flow systems provide significant advantages to cell processing technologies. However, there may be situations where it may be beneficial to execute a process in batch mode (e.g., perform a process in a batch, and move that batch to a subsequent stage once the entire batch is complete, etc.). As needed, continuous and batch processing can both be employed within a single system by holding product from one step in a reservoir prior to its being passed into a subsequent batch process. In some implementations, such batch processing reservoirs can be disposed between separate lateral layers or lateral stacks of parallel layers, that each defines a stage in a batch processing portion. That is, scaling of both continuous flow systems and batch processing systems can be scaled using parallel and lateral layer arrangements.

Multiple microfluidic devices (e.g., the modules 200, 300, 400, any other microfluidic features described herein, etc.) can be connected on a single layer via one or more microfluidic multiplexers. The microfluidic multiplexers can be used in a layer to define multiple paths between interconnected networks of microfluidic channels, and can be used to define one or portions or paths of the process flow system 500 described herein above in conjunction with FIGS. 5A, 5B, and 5C. Microfluidic multiplexers can include one or more junctions, inlets, and outlets, and can be used to route fluids from multiple microfluidic channels throughout one or more layers.

Figure 6:
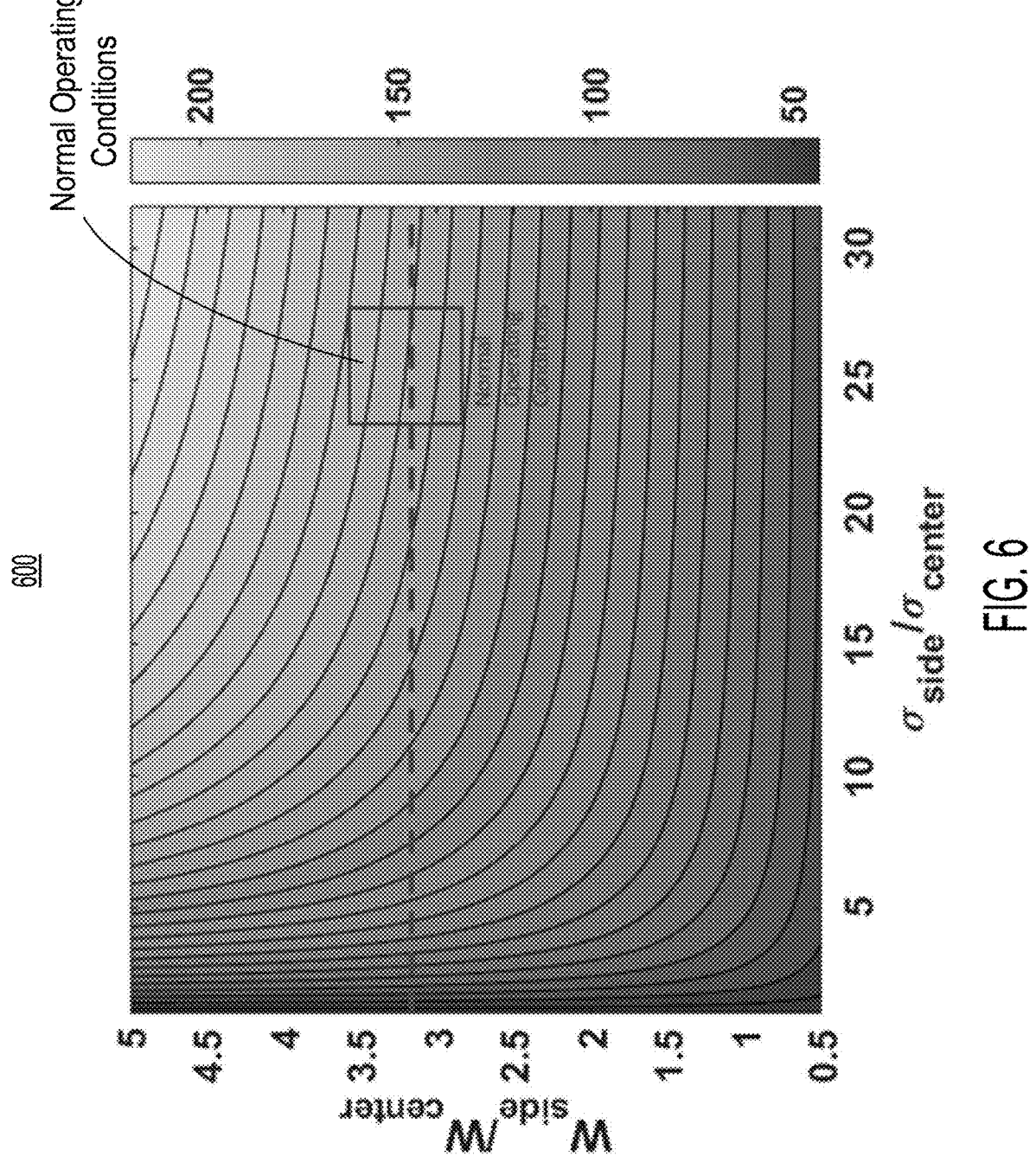
FIG. 6 illustrates a graph showing the electric field experienced by cells in the module of FIG. 4, in accordance with one or more implementations.

FIG. 6 illustrates a graph 600 showing the electric field experienced by cells in the module 400 of FIG. 4. Generally, the electric field delivered to the cells can be affected by the relative conductivity of the side stream solutions compared to the center stream solution, as well as the relative flow rate of the side streams compared to the center stream, which can determine the width of the side streams compared to the center stream. A higher conductivity ratio can result in more voltage dropped across the center stream, and a higher electric field magnitude. A higher flow rate ratio can narrow the center stream, decreasing the distance over which voltage is dropped across the cells, and increasing the electric field magnitude. The graph 600 shows the electric field magnitude experienced by the cells for an applied voltage of 65 V in one implementation of the electroporation module that has a channel width of 1.5 mm. The dashed line in the graph 600 indicates an example flow ratio at which the module 400 can be operated, and the box indicates the range of electric field magnitudes that can be useful for delivering mRNA to primary human T cells. The graph 600 does not consider the effects of diffusion, which can add spatial non-uniformities to the electric field. This can form the framework for one possible feedforward control mechanism, in which conductivity is measured and flow rates are adjusted to achieve the desired electric field. Such control mechanisms are described further below.

FIGS. 7A-7D illustrate block diagrams of example control systems for controlling the electric field experienced by cells in the module 400 of FIG. 4. The magnitude of the electric field applied to the cells in the module 400 can be an important parameter. The electric field magnitude can depend on the applied voltage, the ratio of the conductivities of the side and cell-laden center flow streams in the module 400, and the width of the cell-laden central fluid stream, which in turn can depend on the ratio of the flow rates of the side and center streams. In some implementations, the applied voltage can be dictated by a user of the module 400 and can be well controlled. The flow rate ratio can also be dictated by the user, and can be well controlled if feedback control mechanisms using flow sensors are implemented. However, in some implementations, the conductivity of the sample stream can vary depending on the preparation of the sample, the amount and type of cargo used, and cell donor. Several different mechanisms for controlling the electric field applied to cells in the module 400 can be used, as shown in FIGS. 7A-7D. Any of the control mechanisms shown in FIGS. 7A-7D can be implemented by the controller 1005 described herein below in conjunction with FIG. 10.

Figure 7A:
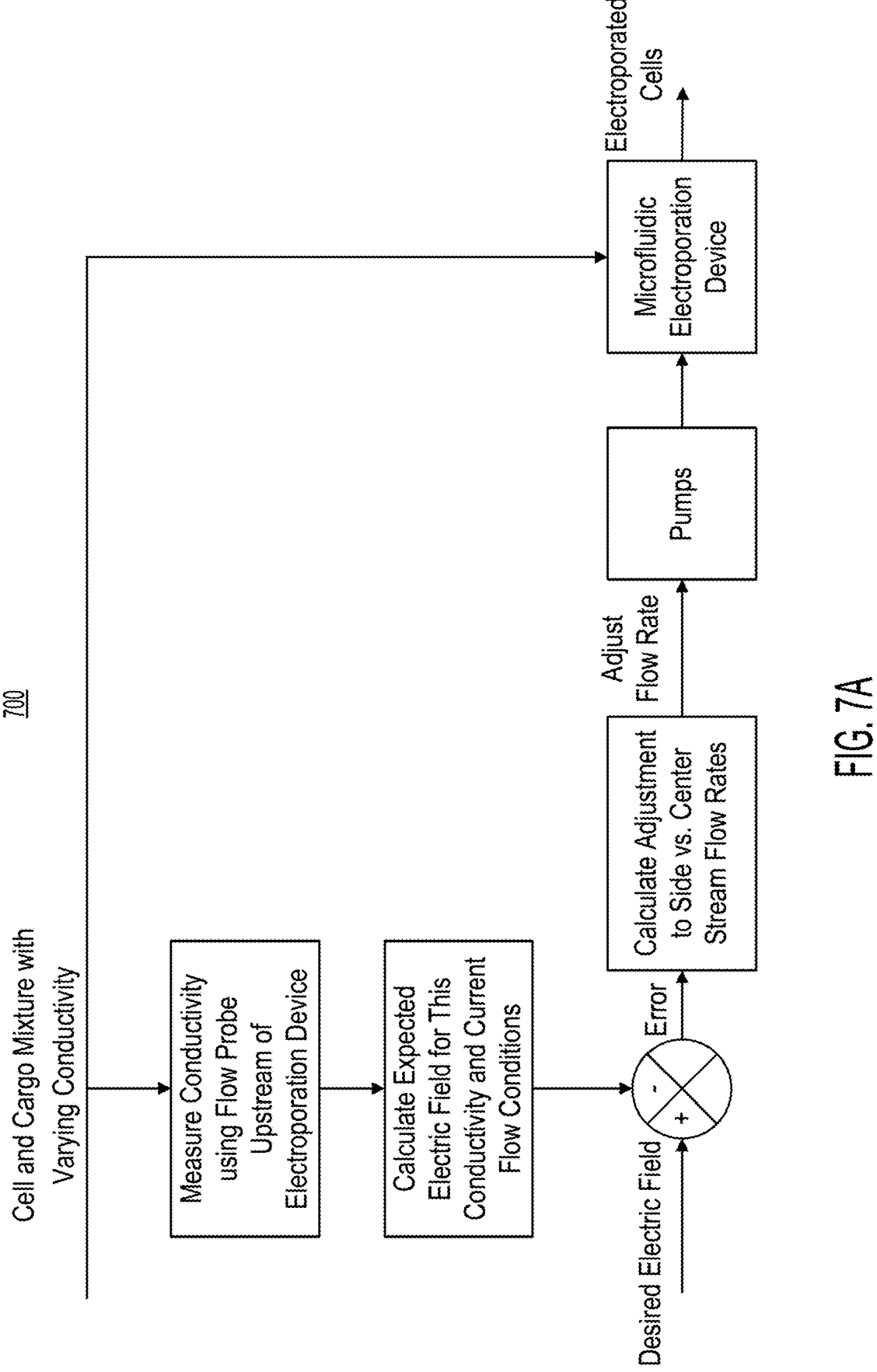
FIGS. 7A-7D illustrate block diagrams of example control systems for controlling the electric field experienced by cells in the module of FIG. 4, in accordance with one or more implementations.
Figure 7B:
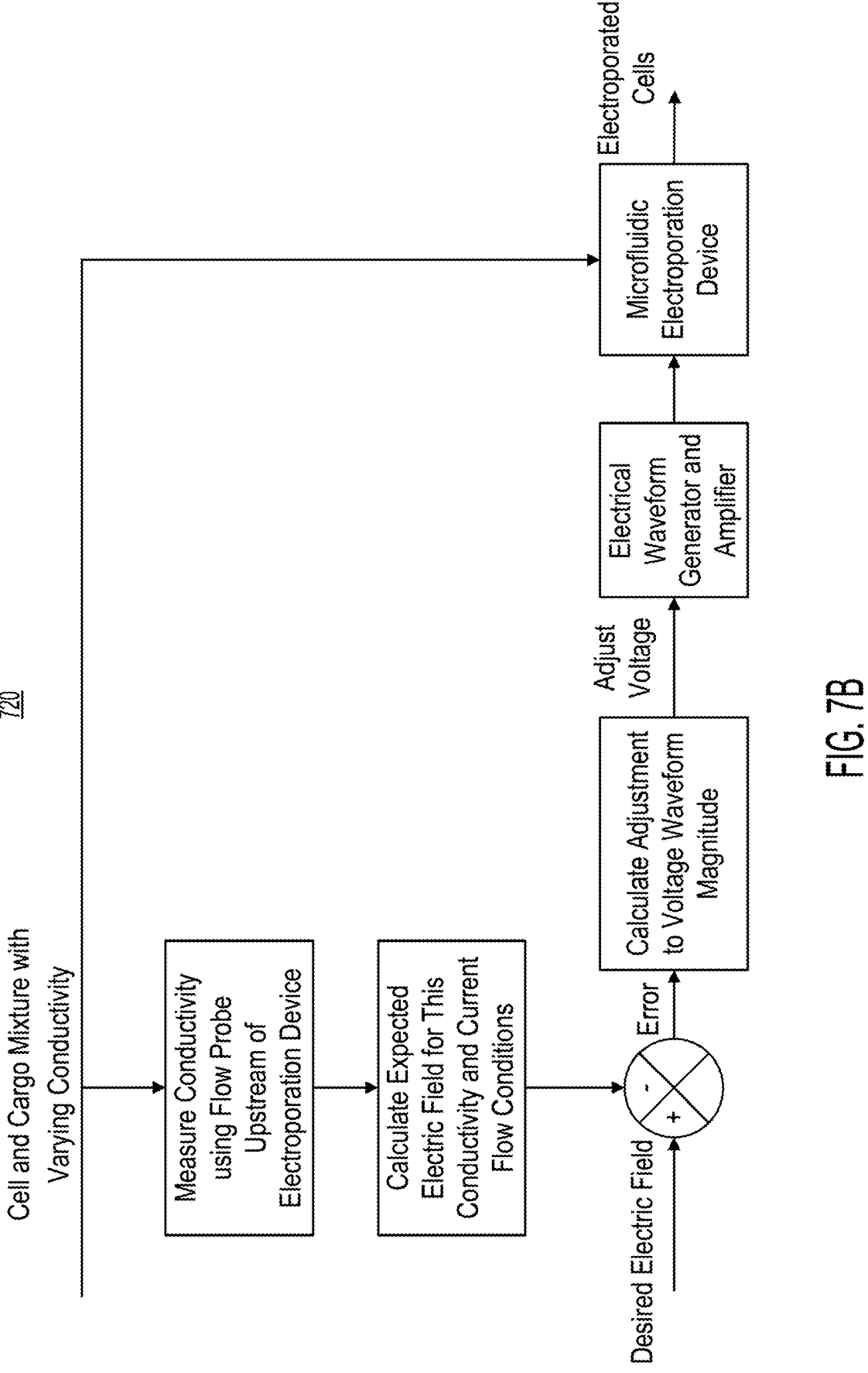

Referring to FIG. 7A, a control system 700 is depicted. The control system 700 is a feed-forward control system, in which the cell and cargo suspension conductivity can be measured upstream of the module 400. Using the control system 700, the ratio of flow rates of the side and center streams can be adjusted in response to conductivity changes to achieve a desired (e.g., predetermined) electric field. Referring to FIG. 7B, a control system 720 is depicted. Like the control system 700 of FIG. 7A, the control system 720 of FIG. 7B is also a feed-forward control system in which the cell and cargo suspension conductivity can be measured upstream of the module 400. Using the control system 720, the applied voltage is adjusted, rather than the flow rates of the side and center streams as shown in the control system 700 of FIG. 7A, to achieve a desired electric field.

Figure 7C:
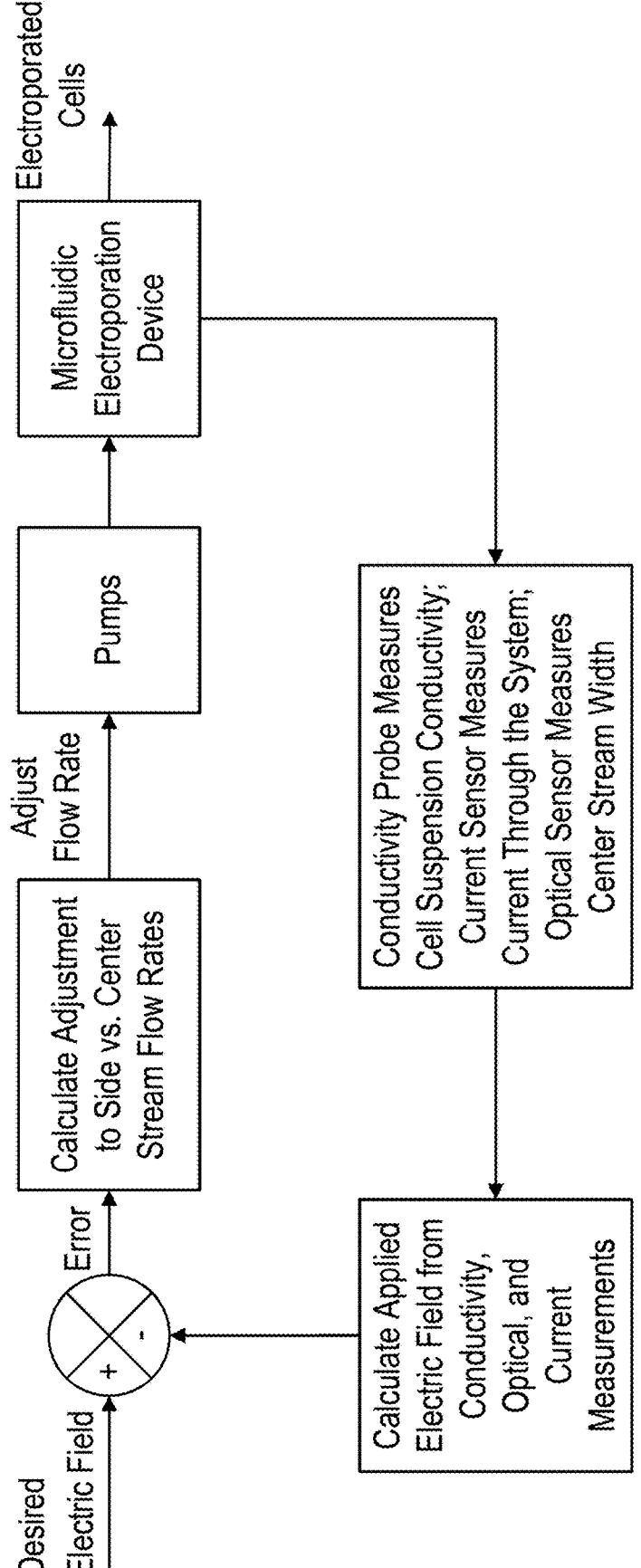
Figure 7D:
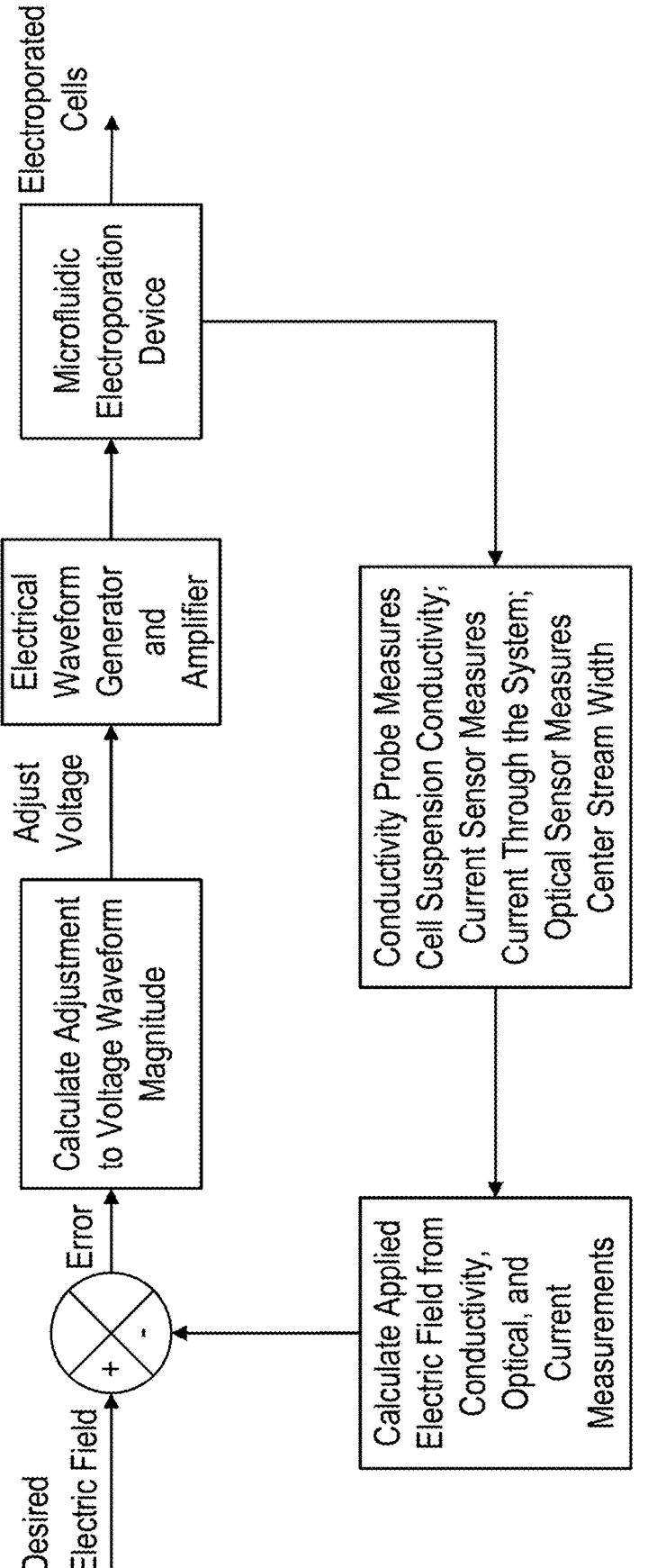

Referring to FIG. 7C, a control system 740 is depicted. The control system 740 is a feedback control system, rather than a feed-forward control system as shown in FIGS. 7A and 7B. Using the control system 700, measurements of the center stream width, solution conductivity, and electrical current in the module 400 can be used to calculate the applied electric field, and the flow rate ratios can be adjusted to reach a desired set point. FIG. 7D shows a control system 760 that also implements feedback control system. Using the control system 760, measurements of the center stream width, solution conductivity, and electrical current in the module 400 can be used to calculate the applied electric field, and the applied voltage (rather than the flow rate ratios) can be adjusted to reach a desired set point.

Figure 10:
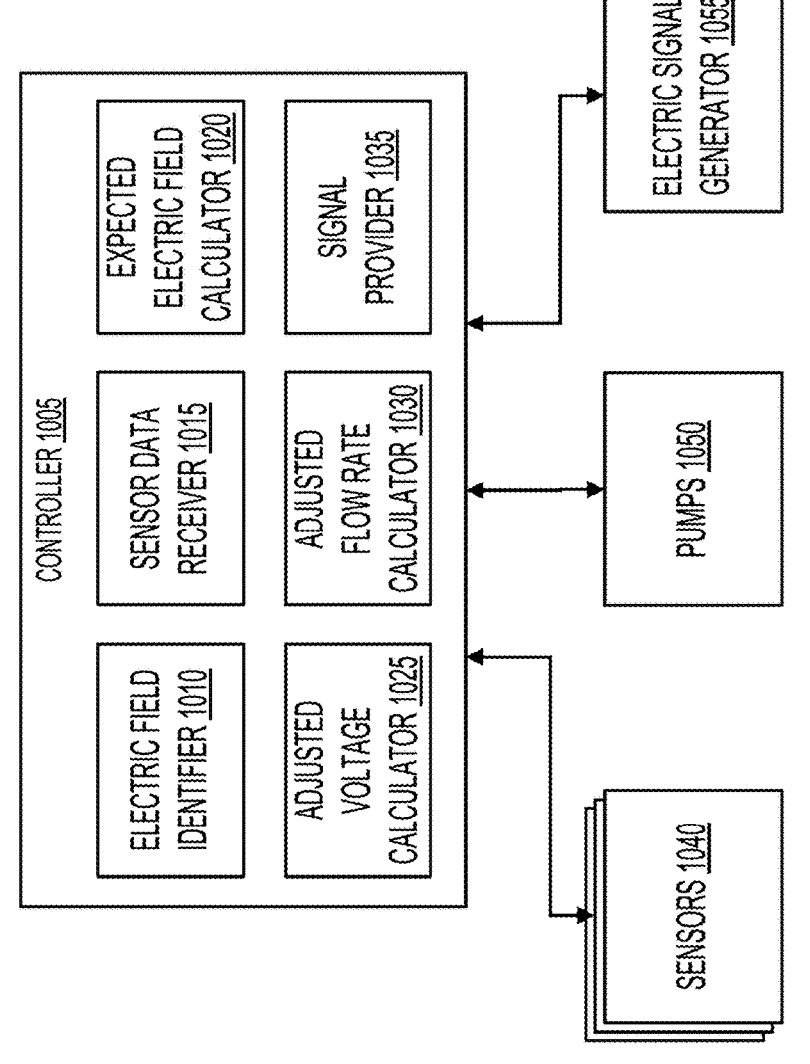
FIG. 10 illustrates a block diagram of an example system for controlling a flow rate or an electric field experienced by fluids flowing in a system similar to that depicted in FIGS. 5A, 5B, and 5C.

In order to account for electric field magnitude changes attendant with changes in sample conductivity, feed-forward or feedback control (or both) of the electric field can be implemented by the systems of FIGS. 7A-7D (e.g., using the controller 1005 depicted in FIG. 10, etc.). In some implementations, the conductivity can be measured upstream of the module 400. In a feed-forward control system, this information can be used to adjust the side and center stream flow rate ratio to narrow or widen the cell-laden center stream, or to adjust the applied voltage, or both. In some implementations, the width of the center stream can be measured directly using optical sensors, and the electrical current through the module 400 can be measured during application of electric field waveforms to cells. In some implementations, conductivity sensors can be placed at the side outlets of the module 400, and a conductivity measurement at the outlet can be used to estimate the width of the center stream. Combined with a measurement of solution conductivity, this information can be used to compute a spatial average of the electric field magnitude delivered to the cells.

In some implementations, the electric field measurement can be used for feedback control. For example, either or both of the side or center flow rate ratio or the applied voltage can be adjusted to approach a desired electric field magnitude set point. In some implementations, sensor electrodes can be integrated into the module 400. For example, such sensor electrodes can be implemented as thin film electrodes positioned on the channel floor. Such sensor electrodes can be used to measure the applied electric field directly. In some implementations, feedback and feed-forward control mechanisms can be used in tandem.

Figure 8:
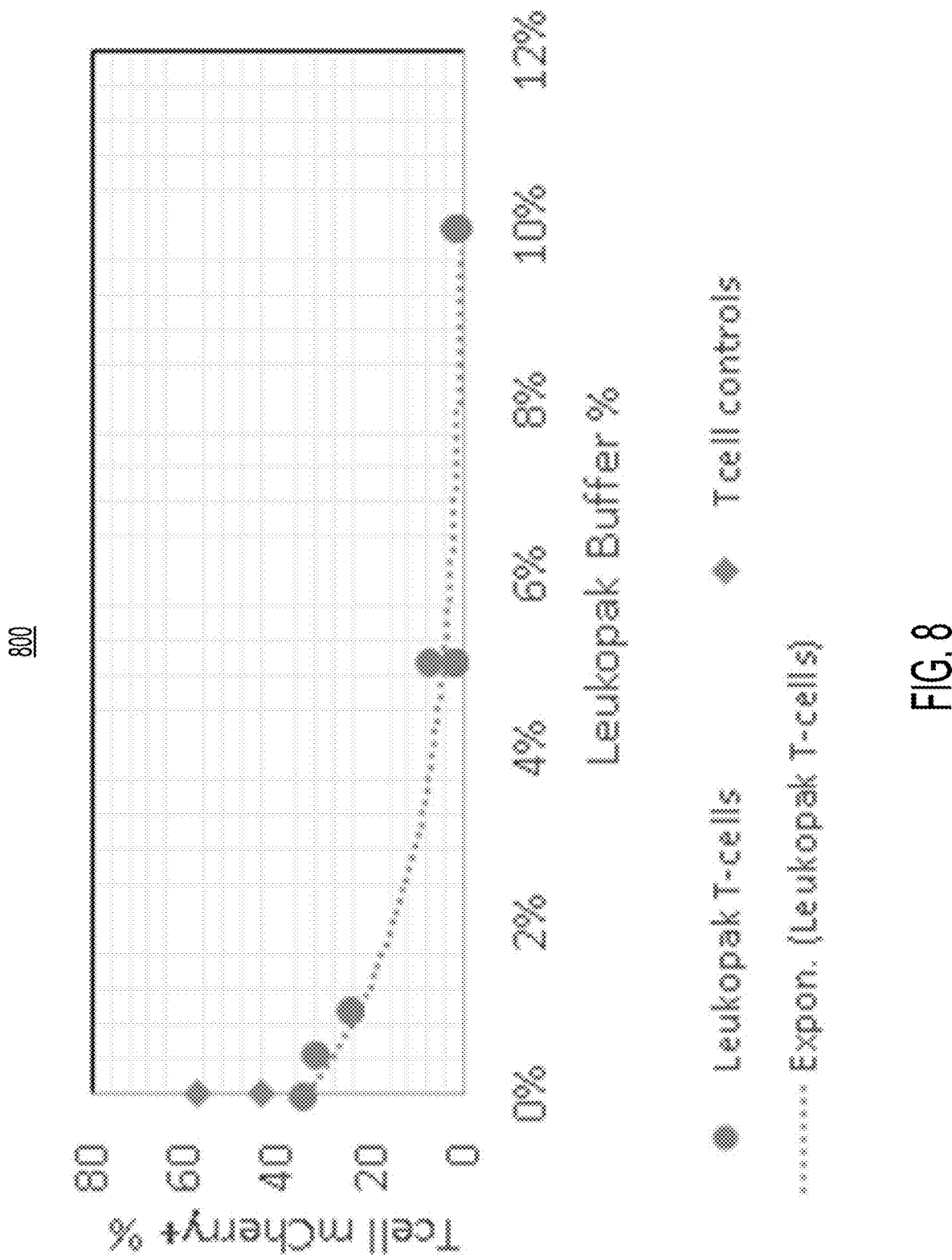
FIGS. 8, 9A, 9B, and 9C illustrate graphs showing experimental results for the system of FIGS. 5A, 5B, and 5C, in accordance with one or more implementations.

To demonstrate functionality of the systems and methods of this disclosure, a leukopak sample (leukapheresis product) was introduced into a system similar to the system 500 shown in FIGS. 5A, 5B, and 5C, and processed to produce lymphocytes that transiently expressed a fluorescent reporter protein known as mCherry. Because the microfluidic electrotransfection module (e.g., the module 400 of FIG. 4) can require that the cells and cargo be suspended in low conductivity media (e.g., approximately 20 times lower than the media used for the sheath streams), target cells were acoustophoretically moved into electroporation media using a module similar to the module 300 prior to electroporation. This reduction in conductivity cannot be accomplished by simply diluting the starting cellular sample in low-conductivity electroporation media as components in the blood product interfere with electrotransfection. A direct dilution approach can require at least a 1:100 ratio of sample to diluent for electrotransfection to be possible, even in commercial bulk electroporation devices that do not explicitly require low-conductivity media, as depicted in the graph 800 of FIG. 8. However, a 1:100 or greater dilution can also reduce the target cell density to 0.25-0.35 M cells/mL. At a flow rate of 1 mL/min, 1 billion cells would require multiple days to process, which in some instances may be an unacceptable level of throughput for processing patient samples for cellular therapy. Thus, an active media exchange step, where cells are resuspended in media for electroporation, can be useful. This is traditionally accomplished in a touch-labor intensive, batch process using centrifugation. To address this technical challenge, this disclosure provides the module 300 shown in FIG. 3 to achieve the exchange automatically and continuously using acoustophoresis.

Figure 9A:
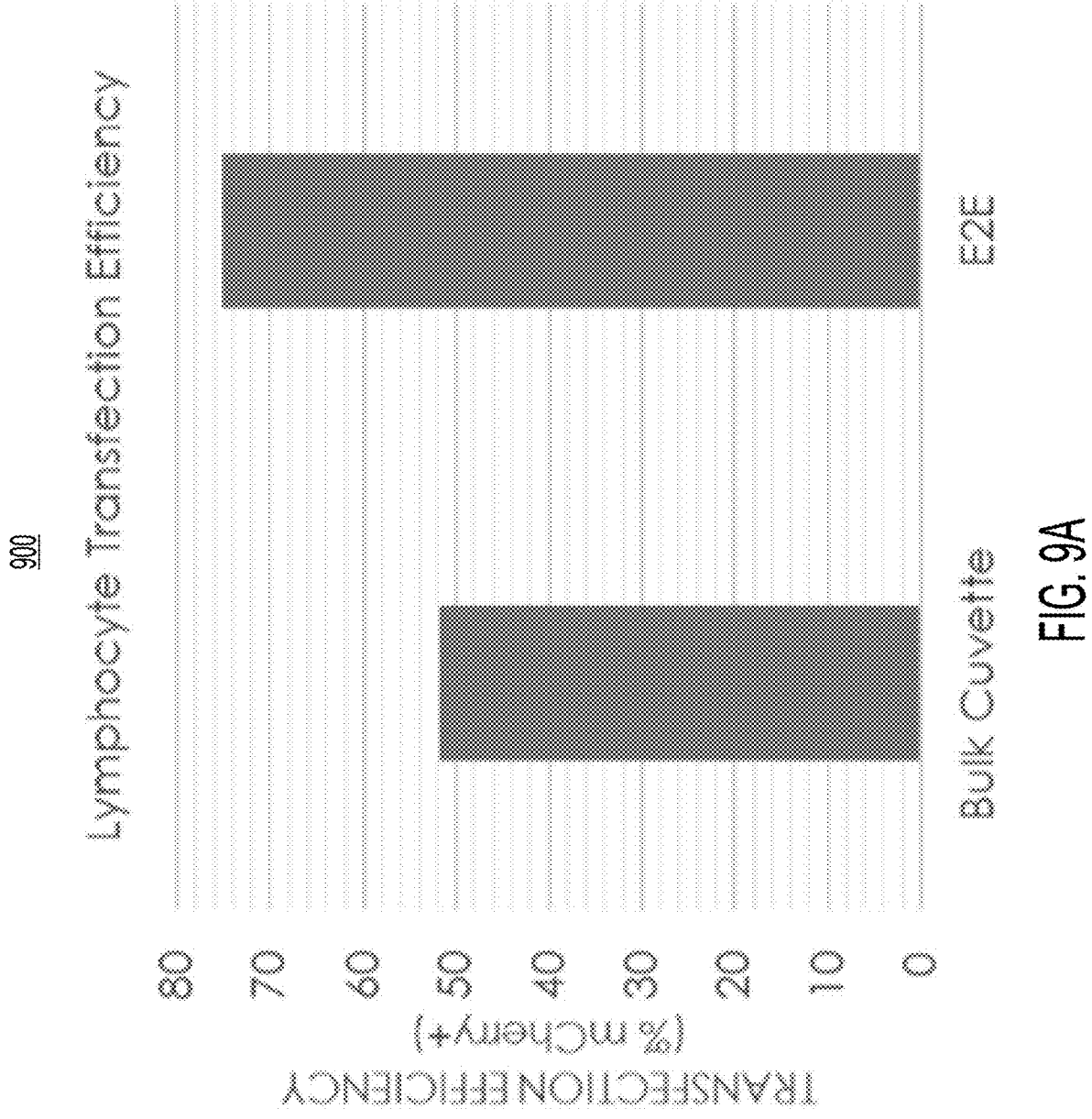
Figure 9B:
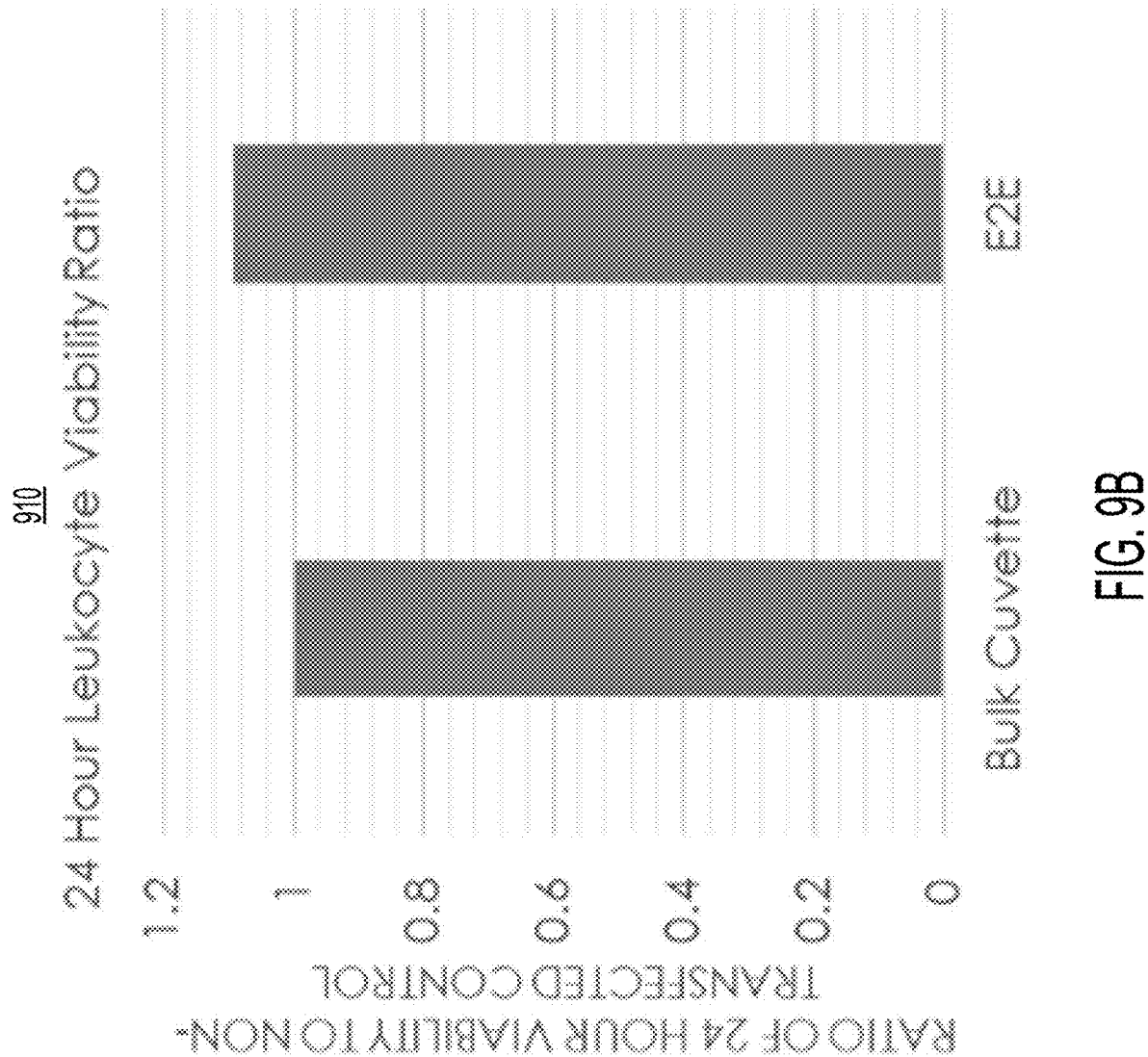
Figure 9C:
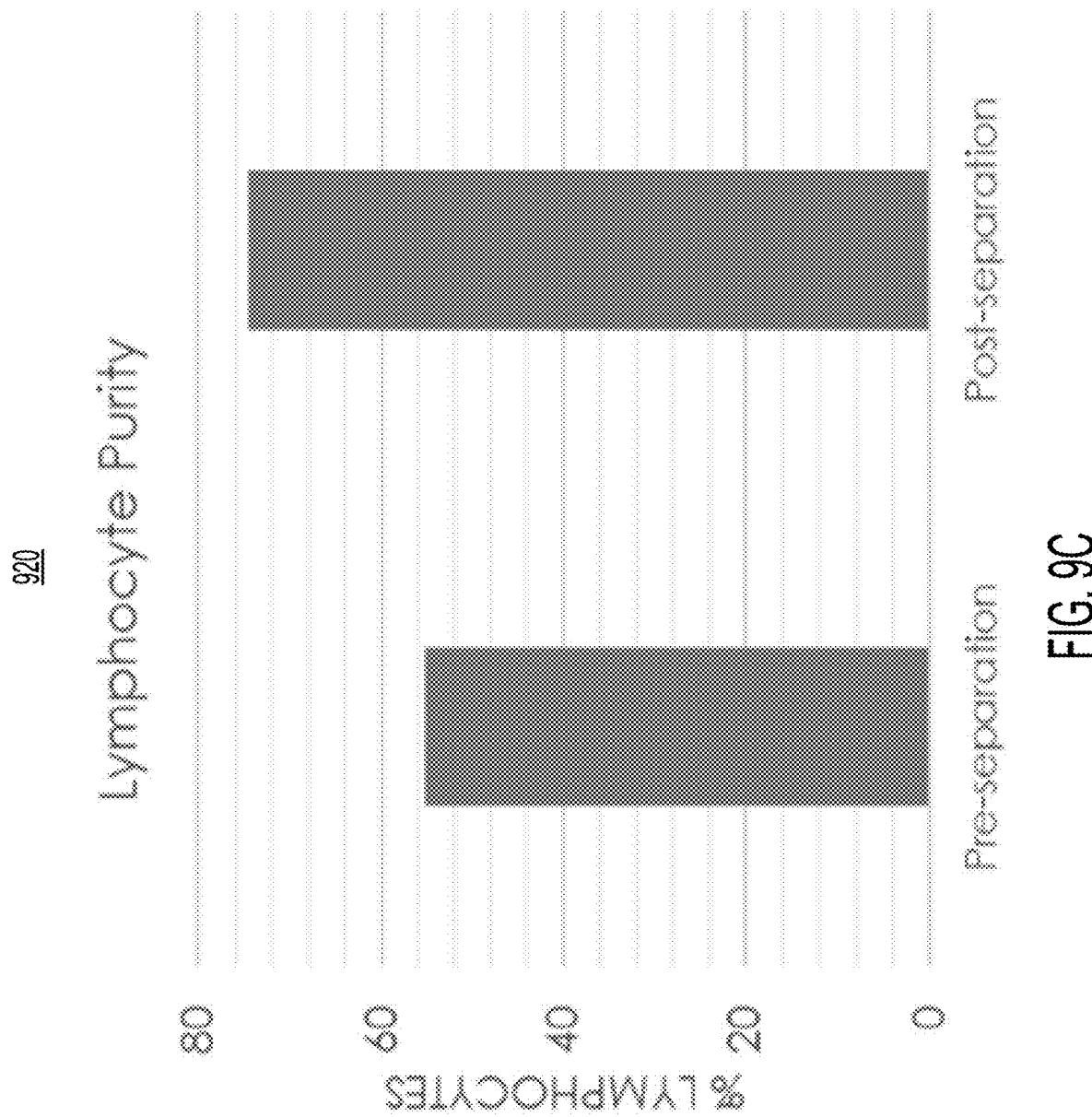

A leukopak sample containing approximately 500 million primary human lymphocytes was processed using the process flow and parameters for the system 500 shown in FIGS. 5A, 5B, and 5C. All components and tubing were sterilized using either autoclave or ethylene oxide and assembled in a biosafety cabinet for sterile operation. Before introduction into the system 500, the leukopak sample was centrifuged and the cells re-suspended in a 1:2 dilution in TexMACS to reduce cell solution gravimetric density, maintain reasonable cell concentration, and reduce processing time and quantities of mRNA needed. The target cells were moved into electroporation buffer containing mCherry-encoding mRNA (32 μg/ml) using the rapid media exchange module 300 shown in FIG. 3, electroporated using the microfluidic electrotransfection module 400 shown in FIG. 4 (three 250-µs pulses at 165 kV/m), and finally enriched for lymphocytes using the microfluidic acoustic apheresis module 200 shown in FIG. 2. The entire process was completed automatically and in continuous flow in approximately 3.5 hours. Transfection efficiency was over 75% and was greater than that of a control sample transfected using a commercial bulk electroporation process, as depicted in the graph 900 of FIG. 9A. In addition, there was no measurable viability reduction relative to the input sample, as depicted in the graph 910 of FIG. 9B, and the lymphocyte population was enriched from about 56% to about 76%, as depicted in the graph 920 of FIG. 9C.

Referring now to FIG. 10, depicted is a block diagram of an example system 1000 for controlling a flow rate or an electric field experienced by fluids flowing in a system similar to the system 500 depicted in FIGS. 5A, 5B, and 5C. The system 1000 can be used to implement the control systems depicted in FIGS. 7A, 7B, 7C, and 7D. The system 1000 can include at least one controller 1005, one or more sensors 1040, one or more pumps 1050, and one or more electric signal generators 1055. The controller 1005 can include at least one electric field identifier 1010, at least one sensor data receiver 1015, at least one expected electric field calculator 1020, at least one adjusted voltage calculator 1025, at least one adjusted flow rate calculator 1030, and at least one signal provider 1035.

Each of the components (e.g., the controller 1005, the sensors 1040, the pumps 1050, etc.) the of the system 1000 can be implemented using the hardware components or a combination of software with the hardware components of a computing system (e.g., computing system 1200 detailed herein in conjunction with FIG. 1200, any other computing system described herein, etc.). Each of the components of the controller 1005 (e.g., the electric signal generator 1055, the electric field identifier 1010, the sensor data receiver 1015, the expected electric field calculator 1020, the adjusted voltage calculator 1025, the adjusted flow rate calculator 1030, the signal provider 1035, etc.) can perform any of the functionalities detailed herein. The controller 1005, or the components thereof, can perform any of the activities described herein above in conjunction with FIGS. 7A, 7B, 7C, and 7D.

The controller 1005 can include at least one processor and a memory, e.g., a processing circuit. The memory can store processor-executable instructions that, when executed by processor, cause the processor to perform one or more of the operations described herein. The processor may include a microprocessor, an application-specific integrated circuit (ASIC), a field-programmable gate array (FPGA), etc., or combinations thereof. The memory may include, but is not limited to, electronic, optical, magnetic, or any other storage or transmission device capable of providing the processor with program instructions. The memory may further include a floppy disk, CD-ROM, DVD, magnetic disk, memory chip, ASIC, FPGA, read-only memory (ROM), random-access memory (RAM), electrically erasable programmable ROM (EEPROM), erasable programmable ROM (EPROM), flash memory, optical media, or any other suitable memory from which the processor can read instructions. The instructions may include code from any suitable computer programming language. The controller 1005 can include any or all of the components and perform any or all of the functions of the computer system 1200 described herein in conjunction with FIG. 12.

The sensors 1040 (sometimes referred to as a "sensor 1040") can be one or more sensors that can transmit or receive data from the controller 1005 or the components thereof. The sensors can include, or be similar to, flow-through conductivity sensor 535 described above in conjunction with FIGS. 5A-5C, flow rate sensors, optical sensors, or other types of sensors as described herein. For example, the sensors 1040 can be the any of the sensors integrated into the system 500, or other similar flow systems, to enable interrogating (e.g., by the components of the controller 1005, etc.) the system 500 for operation faults and feedback or feed-forward control mechanisms. For example, sensors can be integrated either as system-wide components, or directly into the modules 200, 300, and 400, or any other modules, reservoirs, valves, or flow structures described herein. Possible sensors that can be integrated into the system 500, or other similar flow systems, include flow sensors for controlling flow rates, conductivity probes, visual measurement of stream widths in sheath flows, and electrical current measurements. In some implementations, optical sensors can also be used to assess the quality of sheath flows used in the system 500, which in turn can be used to adjust flow rates as needed to generate the correct, stable flows. In some implementations, optical sensors can also be used to calibrate and tune the acoustophoretic modules, in which the optimal driving frequency for the piezoelectric components can be determined automatically by observing the concentration of cells in one of the outlet fractions.

The sensors 1040 can include one or more absorbance or impedance sensors that can also be incorporated into the system 500, or other similar flow systems, for real-time estimates of either or both of cell concentration or cell density. This can provide information on processing throughput in the system 500 to the components of the controller 1005, and can be used determine where there may be losses in the system 500, or other similar flow systems, if cell recovery is low. Information from measurements of cell concentration can be used in closed loop control to adjust flow rates in the inlets or outlets of the modules 200, 300, and 400, to adjust acoustic power or frequency, or to adjust automated addition of reagents in the system 500, or in other similar flow systems.

The sensors 1040 can be added to any of the modules described herein (e.g., the modules 200, 300, and 400, etc.) or to locations in a fluid system (e.g., the system 500, etc.) between said modules, to indicate operational quality or efficiency of the flow system and the modules therein. For example, the sensors 1040 can be added to a separation module (e.g., module 200, etc.), or at a point in the system downstream from the separation module, to indicate or detect an efficiency of the acoustophoretic separation of cells that occurs in the separation module. Such sensors can be configured to identify cells within the fluid during or subsequent to the fluid passing through the separation module. In some implementations, sensors can be added to an electroporation module (e.g., the module 400, etc.), or at a point downstream from the electroporation module, to indicate an efficiency of the transfection that occurs as a result of the operation of the electroporation module. Such a sensor 1040 can determine how much cargo has been introduced into the cells of the fluid sample via the electrotransfection operation performed by the module 400. In some implementations, sensors can be included in the system 500 to monitor cell viability. The sensors 1040 can include a conductivity probe that measures the conductivity of a fluid as the fluid flows through an electroporation device, such as the module

400. The sensors 1040 can include a current sensor that measures an electric current passing through a fluid as the fluid flows through an electroporation device, such as the module 400. The sensors 1040 can include an optical sensor that measures a width of a center portion of the fluid as the fluid through an electroporation device, such as the module 400.

The sensors 1040 can provide real-time outputs to the controller 1005 or the components therein via one or more communication interfaces. The information received from the sensors 1040 can be used as part of a feedback or feed forward control mechanism. For example, based on the outputs of such sensors, adjustable parameters of any of the modules 200, 300, and 400 (e.g., fluid flow rates, fluid sample ratios, applied voltages or electric fields, etc.) can be controlled. Thus, real-time information relating to elec- trotransfection efficiency, separation efficiency, or cell viability can be incorporated into control data to alter the operational characteristics of the system 500, or similar fluid systems, during cell processing The pumps 1050 can cause fluid to flow through one or more pipes or channels in a fluid flow system, such as the system 500 described herein in conjunction with FIGS. 5A-5C. The pumps 1050 can include, for example, the pump 510, the pump 525, the pump 540, the pump 550, the pump 555, or the pump 570 described herein above in conjunction with FIGS. 5A-5C. The pumps 1050 can be peristaltic pumps, or any other type of pump described herein. The pumps 1050 can be used to transport fluids throughout a fluid system similar to the system 500 depicted in FIGS. 5A-5C. The pumps 1050 can be coupled with one or more fluid connectors, fluid reservoirs, fluid capacitors, or other fluid. The rate at which the pumps 1050 transport fluid can be governed by signals received from a controller, such as the controller 1005 (or the components thereof). For example, signals from the controller 1005 can cause one or more of the pumps 1050 to flow fluid at a desired flow rate. The desired flow rate can be indicated in the signal received from the controller 1005. The signal could be a voltage signal causes a peristaltic pump to actuate, or another type of signal that can modulate or control the rate at which one or more of the pumps 1050 can transport fluid.

The electric signal generator 1055 can be a part of the module 400 described herein above in conjunction with FIG. 4. For example, the electric signal generator 1055 can generate a desired voltage across the electrodes 435A and 435B described herein above. The desired voltage can be indicated by a signal received from the controller 1005 (or the components thereof). The electric signal generator 1055 can be a voltage source, such as a direct-current (DC) voltage source or an alternating-current (AC) voltage source. In some implementations, the electric signal genera- tor 1055 can be a current source, such as a DC source or an AC source. The electric signal generator 1055 can be electrically coupled to one or more electrodes, such as the electrodes 435A and 435B. The electric signal generator 1055 can create a voltage difference across the one or more electrodes, forming an electric field. When the electrodes are coupled to one or more fluid channels, as in the module 400 of FIG. 4, the electric signal generator 1055 can create an electric field in the fluid flowing through the module. In some implementations, voltage applied by the electric signal generator can take the form of a sinusoid with a period ranging from 10 ns to 10 ms. In some implementations, the voltage applied by the electric signal generator can take the form of a pulse train with pulse widths ranging from 10 ns to 10 ms. In some implementations, the magnitude of the voltage applied by the electric signal generator 1055 can vary so as to generate an electric field across the center stream that ranges from about 2-600 kV/m, with pulse widths ranging from 10 ns to 10 ms. However, it should be understood that other electric field pulse types, voltage magnitudes, and electric field magnitudes are possible.

Referring now to the functionality of the controller 1005, the electric field identifier 1010 can identify a desired electric field magnitude to induce in the fluid flowing through an electroporation device. Identifying a desired electric field can include receiving a desired electric field from one or more external sources, such as a user input via an input interface, from a configuration file loaded into the memory of the controller 1005, or from an internal setting (e.g., hardware setting such as a jumper, etc.). In some implementations, the desired electric field can be stored as a variable in one or more data structures in the memory of the controller 1005. In fluid systems having more than one electroporation device (e.g., more than one module 400, etc.), the electric field identifier 1010 can identify desired electric field magnitude values for each of the electropora- tion devices. In such implementations, each of the desired electromagnetic field magnitude values can be stored in one or more data structures in association with an identifier of the electroporation device to which the magnitude value corresponds.

The sensor data receiver 1015 can receive sensor values, including the conductivity or a flow rate of the fluid flowing into or through an electroporation device, from the sensors 1040. The sensor data receiver 1015 can receive one or more signals from the sensors 1040 that represent numerical values of a conductivity of a fluid, a flow rate of a fluid, or other sensor data, among others. In some implementations, the sensor data receiver 1015 can ping or query one or more of the sensors 1040 on a predetermined basis, in response to a user input, based on a periodic schedule, or another type of sensor querying procedure. In response to the queries, the sensors can send or transmit, via one or more communica- tion interfaces, sensor information including numerical val- ues representing a physical property of a fluid (e.g., a width of a central channel, an electric current flowing through a fluid, a flow rate of a fluid in a pipe or channel, a flow rate through any of the module 200, the module 300, or the module 400, as described herein, etc.), or other properties of a fluid system (e.g., the system 500, etc.). The sensor information received from the sensors 1040 by the sensor data receiver 1015 can be stored in one or more data structures in the memory of the controller 1005. The sensor information can be stored with various identifiers, for example, a timestamp corresponding to the time the sensor measurement was taken or received, or an identifier of a sensor 1040 that provided the sensor measurement, among others.

The expected electric field calculator 1020 can determine an expected electric field magnitude in the fluid as the fluid flows through the electroporation device. The expected electric field can be calculated based on the conductivity of the fluid streams in the electroporation device and the voltage generated by the electric signal generator. For example, an electric field strength can be calculated using Ohm's law to determine an expected electric field magnitude experienced by the fluid flowing through the electroporation device (e.g., the module 400 described herein in conjunction with FIG. 4, etc.). As depicted in FIG. 4, the module 400 can receive a center stream and two side streams as input. In a non-turbulent flow, the fluids received into the central chan- nel 430 from each input channel may not mix, and instead maintain a stream shape that corresponds to the streams as they are input to the module 400. The conductivity of each fluid can differ. For example, the cell solution in the electroporation buffer (e.g., in the central channel, etc.) can have a lower conductivity than the buffer solution provided by the side channels.

When a voltage potential is applied to the central channel, each fluid stream (e.g., the fluid stream received from the central inlet 410, the buffer solutions received by the side inlets 415a and 415b, etc.) can experience a different voltage drop across its width, and therefore experience different electric fields. An electric field magnitude can be calculated using the electric field equation $$E = \frac{V_{AB}}{d},$$

where E is the electric field magnitude, $V_{AB}$ is the voltage drop across a fluid stream, and d is the width of the fluid stream. As the buffer solution received from the side channels is highly conductive, it can be assumed that the voltage drop experienced across the central channel (e.g., the channel containing cells to be electroporated, etc.) can be about equal to the voltage drop across the electrodes.

Therefore, in some implementations, the voltage provided by the electric signal generator 1055 can be known, and calculating the electric field would be based on the width of the central stream in the electroporation device (or the width of one or more other channels, in some implementations). As described herein, the width of the central stream as it flows through the central channel 430 can be a function of the ratio of the flow rates of the side channels to the flow rate of the center stream. Thus, the width of the central stream can be estimated using the ratio of the flow rates of the side channels to the flow rate of the center stream. The width can be used in the above equation with the known voltage across the electrodes 415a and 415b to calculate the expected electric field magnitude. As described herein above, the flow rates of the side channels and of the central stream can be received, for example, from one or more of the sensors 1040. In some implementations, the voltage drop experienced by the fluids in the central chamber can change based on the relative conductivity of the fluids received from the side channels 415a and 415b, and the fluid received from the central channel 420. If the conductivity of the fluids entering the central channel is known (e.g., received from one or more of the sensors 1040), the voltage drop across the central stream can be calculated using a voltage divider equation. The voltage drop can then be used in the equation above, with the estimated width of the central stream, to calculate the expected electric field magnitude experienced by the central stream in the module 400.

In some implementations, the expected electric field calculator 1020 can determine the expected electric field magnitude based on a conductivity of a fluid flowing through an electric field, the electric current producing the electric field, and a width of a center stream of the fluid. For example, the module 400 includes a center portion of a fluid introduced to a central channel 430 via a central inlet 410. In some implementations, one or more of the sensors 1040 (e.g., optical sensors, etc.) can provide values that correspond to the width of the central stream, the conductivity of the central stream and the side streams, and the current flowing through the central stream and the side streams. Using these values, the expected electric field strength can be calculated.

For example, the voltage drop across the central stream and the side streams can be calculated by dividing the amount of current flowing through the streams by the conductivity values for the respective streams. Using the width value received from the optical sensor with the equation above, the electric field strength experienced by the central stream as it flows through the module 400 can be calculated. The expected electric field experienced by the central channel (or by other fluids flowing through the module 400) can be stored in one or more data structures in the memory of the controller 1005.

The adjusted voltage calculator 1025 can calculate an adjusted voltage for the electric signal generator based on the expected electric field magnitude and the desired electric field magnitude. The adjusted voltage calculator 1025 can calculate a difference between the electric field magnitude experienced by the fluid flowing through the module 400 and the desired electric field magnitude (e.g., by subtraction, etc.). In some implementations, the adjusted voltage calculator 1025 can calculate the percentage difference between the expected electric field magnitude and the desired electric field magnitude. Because the electric field is proportional to the voltage drop across the central stream in the module 400, the adjusted voltage calculator 1025 can calculate the adjusted voltage by multiplying the current voltage setting of the electric signal generator 1055 by the percentage difference. For example, if the desired electric field strength is 200% of the expected (e.g., estimated) electric field strength in the central stream, the adjusted voltage calculator 1025 can calculate the adjusted voltage as $2.00 * V_c$, where $V_c$ is the current voltage setting of the electric signal generator. In some implementations, the controller can adjust the voltage within a set of operating conditions, such as the operating conditions depicted in FIG. 6.

The adjusted flow rate calculator 1030 can calculate an adjusted flow rate for one or more fluid flows entering an electroporation device, such as the module 400, based on a conductivity value, the electric current in the electroporation device, and a width of the center portion of the fluid. In some implementations, the adjusted flow rate calculator 1030 can calculate an adjusted flow rate for at least one of the first fluid or the second fluid based on at least one of the first flow rate or the second flow rate. The adjusted flow rate calculator 1030 can determine an adjusted flow rate to one or more of the central stream or the side streams received by the central channel 430 of the module 400. As described herein, the width of the central channel can be inversely proportional to the electric field strength experienced by the central channel. Further, the width of the central channel can be a function of the ratio of the flow rates of the side streams to the flow rate of the central stream. Therefore, in some implementations, the adjusted flow rate calculator 1030 can calculate the adjusted flow rate for the side streams, by increasing or decreasing the flow rate of the side streams, to change the width of the central stream. For example, if the expected electric field magnitude is less than the desired electric field magnitude, the adjusted flow rate calculator 1030 can increase the flow rates of the side streams. In some implementations, the adjusted flow rate calculator 1030 can decrease the flow rate of the central stream to increase the expected electric field magnitude. Likewise, if the expected electric field magnitude is greater than the desired electric field magnitude, the adjusted flow rate calculator 1030 can decrease the flow rate of the side streams. In some implementations, the adjusted flow rate calculator 1030 can increase the flow rate of the central stream to decrease the expected electric field strength.

In some implementations, the adjusted flow rate calculator 1030 can adjust both the central stream flow rate and the side stream flow rate (e.g., decrease the central stream flow rate and increase the side stream flow rate, increase the central stream flow rate and decrease the side stream flow rate, increase both the central stream flow rate and the side stream flow rate, decrease both the central stream flow rate and the side stream flow rate, etc.). The adjusted values of the flow rates calculated by the adjusted flow rate calculator 1030 can be stored, for example, in one or more data structures in the memory of the controller 1005. In some implementations, each adjusted flow rate value can be stored in association with an identifier of a pump that controls the flow rate that is being adjusted. It should be understood that the flow rate values adjusted by the adjusted flow rate calculator 1030 correspond to values stored in the memory of the controller 1005 that are used to determine the speed or frequency that the pumps 1050 transmit fluid through the fluid system (e.g., the system 500, etc.).

The signal provider 1035 can provide one or more signals representing the adjusted voltage to the electrical signal generator 1055. The signals can cause the electric signal generator 1055 to generate a voltage in the electroporation device. For example, the signals can include an indication to increase, or decrease, the magnitude of one or electric signals generated by the electric signal generator. In some implementations, the signal can be an analog signal representing a value that is proportional to the adjusted voltage value calculated by the adjusted voltage calculator 1025. In some implementations, the signal can be a digital signal representing a value that is proportional to the adjusted voltage value calculated by the adjusted voltage calculator 1025. The signals generated and transmitted by the signal provider 1035 can be transmitted in real-time as the adjusted values are calculated by the adjusted voltage calculator 1025 or the adjusted flow rate calculator 1030. In some implementations, the signal provider 1035 can control the frequency that the electric signal generator 1055 generates electric pulses through the central channel 430 of the module 400.

The signal provider 1035 can provide a second signal representing the adjusted flow rate to a pump that controls the flow of the first fluid (e.g., the fluid in the side streams, etc.) or the second fluid (e.g., the fluid in the central stream), causing the first fluid or the second fluid to flow at a second, adjusted flow rate. For example, the signal provider 1035 can access the memory of the controller 1005 to retrieve the adjusted flow rate values for each of the side streams and the central stream. In some implementations, the signal provider 1035 can retrieve the adjusted flow rate values as they are generated by the adjusted flow rate calculator 1030. The signal provider 1035 can transmit the signals to the one or more pumps 1050, causing the pumps 1050 to actuate and transmit fluid through the central channel 430 of the module 400 at the adjusted flow rates calculated by the adjusted flow rate calculator 1030. In some implementations, the signal can be an analog signal representing a value that is proportional to the adjusted flow rate values (e.g., for one or more of the side streams or the central stream, etc.) calculated by the adjusted flow rate calculator 1030. In some implementations, the signal can be a digital signal representing a value that is proportional to the adjusted flow rate values calculated by the adjusted flow rate calculator 1030. In some implementations, the signal provider 1035 can control the pumps 1050 (e.g., transmit signals that cause the pumps 1050 to actuate periodically, etc.). In such implementations, the frequency that the signal provider 1035 transmits signals to the pumps 1050 to cause the pumps 1050 to actuate can be based on the adjusted flow rate values.

Referring now to FIG. 11, depicted is a flow diagram of an example method 1100 for controlling a flow rate or an electric field experienced by fluids flowing in a system similar to that depicted in FIGS. 5A, 5B, and 5C. The method can be performed, for example, by a controller device (e.g., the controller 1005, the computer system 1200, etc.). In brief overview of the method 1100, the method 1100 can include identifying a desired electric field magnitude (BLOCK 1102), receiving a conductivity of a fluid flow through an electroporation device (e.g., the module 400, etc.) (BLOCK 1104), determining an expected electric field magnitude in a fluid flowing in the electroporation device (BLOCK 1106), calculating an adjusted voltage for the electric signal generator (BLOCK 1108), providing a signal representing the adjusted voltage to an electric signal generator (BLOCK 1110).

In further detail of the method 1100, the method 1100 can include identifying a desired electric field magnitude (BLOCK 1102). Identifying a desired electric field can include receiving a desired electric field from one or more external sources, such as a user input via an input interface, from a configuration file loaded into the memory of the controller, or from an internal setting (e.g., hardware setting such as a jumper, etc.). In some implementations, the desired electric field can be stored as a variable in one or more data structures in the memory of the controller. In fluid systems having more than one electroporation device (e.g., more than one module 400, etc.), the controller can identify desired electric field magnitude values for each of the electroporation devices. In such implementations, each of the desired electromagnetic field magnitude values can be stored in one or more data structures in association with an identifier of the electroporation device to which the magnitude value corresponds.

The method 1100 can include receiving a conductivity of a fluid flow through an electroporation device (e.g., the module 400, etc.) (BLOCK 1104). The controller can receive one or more signals from sensors (e.g., the sensors 1040, etc.) that represent numerical values of a conductivity of a fluid, a flow rate of a fluid, or other sensor data, among others. In some implementations, the controller can ping or query one or more of the sensors on a predetermined basis, in response to a user input, based on a periodic schedule, or another type of sensor querying procedure. In response to the queries, the sensors can send or transmit, via one or more communication interfaces, sensor information including numerical values representing a physical property of a fluid (e.g., a width of a central channel, an electric current flowing through a fluid, a flow rate of a fluid in a pipe or channel, a flow rate through any of the module 200, the module 300, or the module 400, as described herein, etc.), or other properties of a fluid system (e.g., the system 500, etc.). The sensor information received by the controller from the sensors can be stored in one or more data structures in the memory of the controller. The sensor information can be stored with various identifiers, for example, a timestamp corresponding to the time the sensor measurement was taken or received, or an identifier of a sensor that provided the sensor measurement, among others.

The method 1100 can include determining an expected electric field magnitude in a fluid flowing in the electroporation device (BLOCK 1106). The expected electric field can be calculated based on the conductivity of the fluid streams in the electroporation device and the voltage generated by the electric signal generator. For example, an electric field strength can be calculated using Ohm's law to determine an expected electric field magnitude experienced by the fluid flowing through the electroporation device (e.g., the module 400 described herein in conjunction with FIG. 4, etc.). As depicted in FIG. 4, the module 400 can receive a center stream and two side streams as input. In a non-turbulent flow, the fluids received into the central channel 430 from each input channel may not mix, and instead maintain a stream shape that corresponds to the streams as they are input to the module 400. The conductivity of each fluid can differ. For example, the cell solution in the electroporation buffer (e.g., in the central channel, etc.) can have a lower conductivity than the buffer solution provided by the side channels.

When a voltage potential is applied to the central channel, each fluid stream (e.g., the fluid stream received from the central inlet 410, the buffer solutions received by the side inlets 415a and 415b, etc.) can experience a different voltage drop across its width, and therefore experience different electric fields. An electric field magnitude can be calculated using the electric field equation $$E = \frac{V_{AB}}{d},$$

where E is the electric field magnitude, $V_{AB}$ is the voltage drop across a fluid stream, and d is the width of the fluid stream. As the buffer solution received from the side channels is highly conductive, it can be assumed that the voltage drop experienced across the central channel (e.g., the channel containing cells to be electroporated, etc.) can be about equal to the voltage drop across the electrodes.

Therefore, in some implementations, the voltage provided by the electric signal generator (e.g., electric signal generator 1055, etc.) can be known, and calculating the electric field would be based on the width of the central stream in the electroporation device (or the width of one or more other channels, in some implementations). As described herein, the width of the central stream as it flows through the central channel 430 can be a function of the ratio of the flow rates of the side channels to the flow rate of the center stream. Thus, the width of the central stream can be estimated using the ratio of the flow rates of the side channels to the flow rate of the center stream. The width can be used in the above equation with the known voltage across the electrodes 415a and 415b to calculate the expected electric field magnitude. As described herein above, the flow rates of the side channels and of the central stream can be received, for example, from one or more sensors in communication with the controller. In some implementations, the voltage drop experienced by the fluids in the central chamber can change based on the relative conductivity of the fluids received from the side channels 415a and 415b, and the fluid received from the central channel 420. If the conductivity of the fluids entering the central channel is known (e.g., received from one or more of the sensors 1040), the voltage drop across the central stream can be calculated using a voltage divider equation. The voltage drop can then be used in the equation above, with the estimated width of the central stream, to calculate the expected electric field magnitude experienced by the central stream in the module 400.

In some implementations, the controller can determine the expected electric field magnitude based on a conductivity of a fluid flowing through an electric field, the electric current producing the electric field, and a width of a center stream of the fluid. For example, the module 400 includes a center portion of a fluid introduced to a central channel 430 via a central inlet 410. In some implementations, one or more sensors (e.g., optical sensors, etc.) can provide values that correspond to the width of the central stream, the conductivity of the central stream and the side streams, and the current flowing through the central stream and the side streams. Using these values, the expected electric field strength can be calculated. For example, the voltage drop across the central stream and the side streams can be calculated by dividing the amount of current flowing through the streams by the conductivity values for the respective streams. Using the width value received from the optical sensor with the equation above, the electric field strength experienced by the central stream as it flows through the module 400 can be calculated. The expected electric field experienced by the central channel (or by other fluids flowing through the module 400) can be stored in one or more data structures in the memory of the controller.

The method 1100 can include calculating an adjusted voltage for the electric signal generator (BLOCK 1108). The controller can calculate an adjusted voltage for the electric signal generator based on the expected electric field magnitude and the desired electric field magnitude. The controller can calculate a difference between the electric field magnitude experienced by the fluid flowing through the module 400 and the desired electric field magnitude (e.g., by subtraction, etc.). In some implementations, the controller can calculate the percentage difference between the expected electric field magnitude and the desired electric field magnitude. Because the electric field is proportional to the voltage drop across the central stream in the module 400, the controller can calculate the adjusted voltage by multiplying the current voltage setting of the controller by the percentage difference. For example, if the desired electric field strength is 200% of the expected (e.g., estimated) electric field strength in the central stream, the controller can calculate the adjusted voltage as 2.00 * $V_C$, where $V_C$ is the current voltage setting of the electric signal generator. In some implementations, the controller can adjust the voltage within a set of operating conditions, such as the operating conditions depicted in FIG. 6.

The controller can calculate an adjusted flow rate for one or more fluid flows entering an electroporation device, such as the module 400, based on a conductivity value, the electric current in the electroporation device, and a width of the center portion of the fluid. In some implementations, the controller can calculate an adjusted flow rate for at least one of the first fluid or the second fluid based on at least one of the first flow rate or the second flow rate. The controller can determine an adjusted flow rate to one or more of the central stream or the side streams received by the central channel 430 of the module 400. As described herein, the width of the central channel can be inversely proportional to the electric field strength experienced by the central channel. Further, the width of the central channel can be a function of the ratio of the flow rates of the side streams to the flow rate of the central stream. Therefore, in some implementations, the controller can calculate the adjusted flow rate for the side streams, by increasing or decreasing the flow rate of the side streams, to change the width of the central stream. For example, if the expected electric field magnitude is less than the desired electric field magnitude, the controller can increase the flow rates of the side streams. In some implementations, the controller can decrease the flow rate of the central stream to increase the expected electric field magnitude. Likewise, if the expected electric field magnitude is greater than the desired electric field magnitude, the controller can decrease the flow rate of the side streams. In some implementations, the controller can increase the flow rate of the central stream to decrease the expected electric field strength.

The method 1100 can include providing one or more signals representing the adjusted voltage to an electric signal generator (BLOCK 1110). The signals can cause an electric signal generator (e.g., the electric signal generator 1055, etc.) to generate a voltage in the electroporation device. For example, the signals can include an indication to increase, or decrease, the magnitude of one or electric signals generated by the electric signal generator. In some implementations, the signal can be an analog signal representing a value that is proportional to the adjusted voltage value calculated by the controller in BLOCK 1108. In some implementations, the signal can be a digital signal representing a value that is proportional to the adjusted voltage value. In some implementations, the controller can control the frequency that the electric signal generator generates electric pulses through the central channel 430 of the module 400.

In some implementations, the controller can provide a second signal representing the adjusted flow rate to a pump that controls the flow of the first fluid (e.g., the fluid in the side streams, etc.) or the second fluid (e.g., the fluid in the central stream), causing the first fluid or the second fluid to flow at a second, adjusted flow rate. The controller can retrieve the adjusted flow rate values as they are generated in BLOCK 1108. The controller can transmit the signals to the one or more pumps (e.g., the pumps 1050, etc.), causing the pumps to actuate and transmit fluid through the central channel 430 of the module 400 at the adjusted flow rates. In some implementations, the signal can be an analog signal representing a value that is proportional to the adjusted flow rate values (e.g., for one or more of the side streams or the central stream, etc.). In some implementations, the signal can be a digital signal representing a value that is proportional to the adjusted flow rate values. In some implementations, the controller can control the pumps (e.g., transmit signals that cause the pumps to actuate periodically, etc.). In such implementations, the frequency that the controller transmits signals to the pumps to can be based on the adjusted flow rate values.

Figure 12:
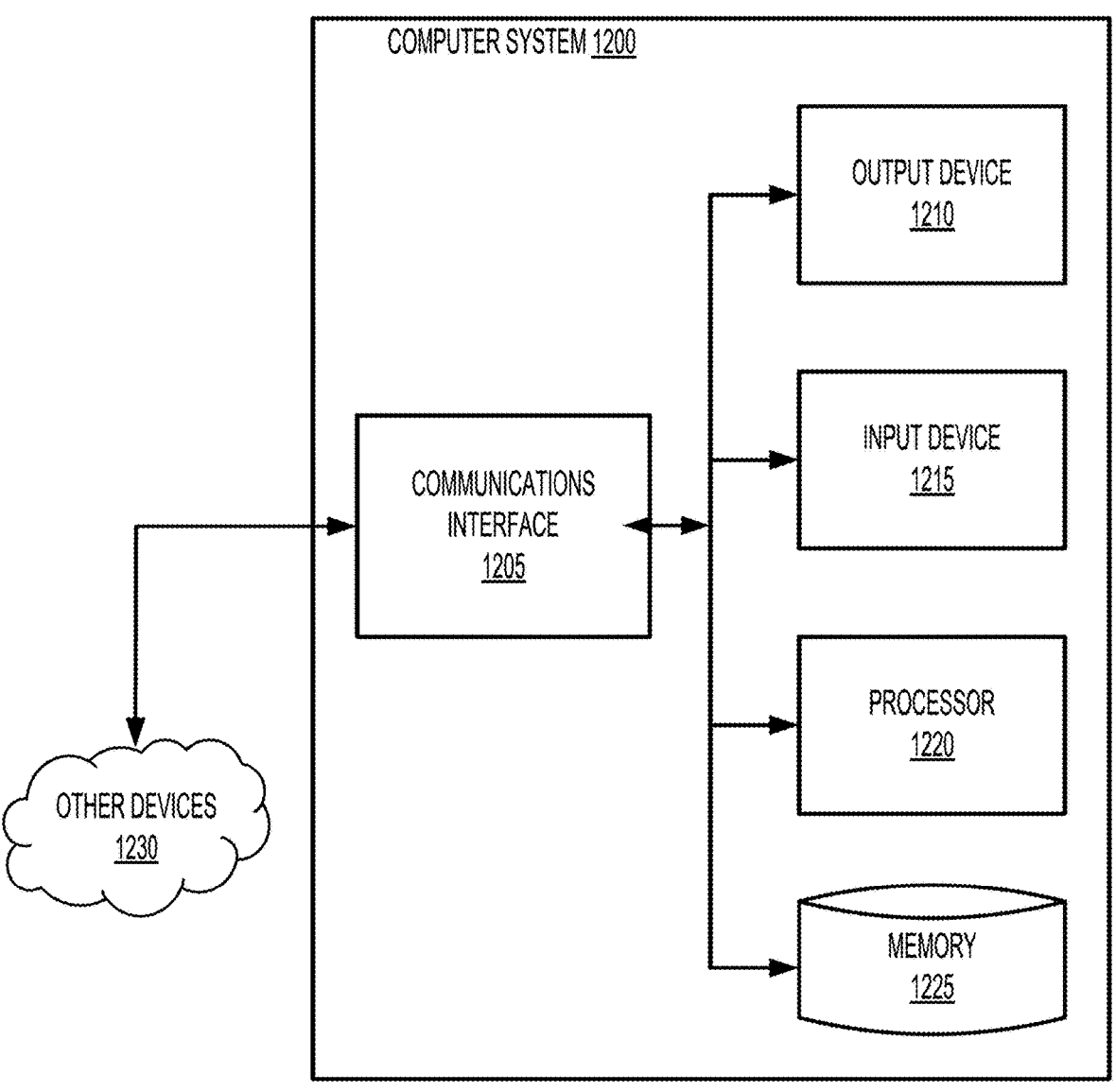
FIG. 12 depicts a block of a general architecture for a computer system that may be employed to implement various elements of the systems and methods described and illustrated herein.

FIG. 12 shows the general architecture of an illustrative computer system 1200 that may be employed to implement any of the computer systems discussed herein in accordance with some implementations. The computer system 1200 can be used to in a control system similar to the system 1000 described herein in conjunction with FIG. 10. The computer system 1200 can control one or more other devices 1230, which can include one or more pumps (e.g., the pumps 1050, any other pumps described herein, etc.), one or more electric signal generators (e.g., the electric signal generators 1055, any other electric signal generators described herein, etc.), or any other type of device or system that can be controlled using one or more signals. The computer system 1200 of FIG. 12 comprises one or more processors 1220 communicatively coupled to memory 1225, one or more communications interfaces 1205, and one or more output devices 1210 (e.g., one or more display units) and one or more input devices 1215. The processors 1220 can be included in any of the computing device described herein.

In the computer system 1200 of FIG. 12, the memory 1225 may comprise any computer-readable storage media, and may store computer instructions such as processor-executable instructions for implementing the various functionalities described herein for respective systems, as well as any data relating thereto, generated thereby, or received via the communications interface(s) or input device(s) (if present). Referring again to the system 1200 of FIG. 12, the computer system 1200 can include the memory 1225 to store information any of the information, variables, vectors, data structures, or other computer-readable information described herein, among others. The processor(s) 1220 shown in FIG. 12 may be used to execute instructions stored in the memory 1225 and, in so doing, also may read from or write to the memory various information processed and or generated pursuant to execution of the instructions.

The processor 1220 of the computer system 1200 shown in FIG. 12 also may be communicatively coupled to or control the communications interface(s) 1205 to transmit or receive various information pursuant to execution of instructions. For example, the communications interface(s) 1205 may be coupled to a wired or wireless network, bus, or other communication means and may therefore allow the computer system 1200 to transmit information to or receive information from other devices (e.g., other computer systems). While not shown explicitly in the system of FIG. 12, one or more communications interfaces facilitate information flow between the components of the system 1200. In some implementations, the communications interface(s) may be configured (e.g., via various hardware components or software components) to provide one or more interfaces (e.g., an application interface, a command-line interface, a website interface, etc.) as an access portal to at least some aspects of the computer system 1200. Examples of communications interfaces 1205 include user interfaces (e.g., web pages), network interfaces, network ports, command-line protocols, or any other type of communication interface through which a user can communicate with the computer system 1200.

The communications interfaces 1205 can include one or more sensor interfaces to transmit and receive information from any sensors described herein, including the sensors 1040 described herein in conjunction with FIG. 10. The communications interfaces 1205 can transmit or receive one or more signals that control the parameters of other systems described herein, including the system 500 or the system 1000. Some example parameters that can be controlled by the computer system 1200 include the flow rate between one or more fluid junctions (e.g., by transmitting signals to one or more pumps to change flow rate of fluids, etc.), or a voltage generated by an electric signal generator (e.g., the electric signal generator 1055, etc.), or any other controllable devices described herein (e.g., valves, etc.).

The output devices 1210 of the computer system 1200 shown in FIG. 12 may be provided, for example, to allow various information to be viewed or otherwise perceived in connection with execution of the instructions. The input device(s) 1215 may be provided, for example, to allow a user to make manual adjustments, make selections, enter data, or interact in any of a variety of manners with the processor during execution of the instructions. Additional information relating to a general computer system architecture that may be employed for various systems discussed herein is provided further herein.

Implementations of some of the subject matter and the operations described in this specification can be implemented in digital electronic circuitry, or in computer software embodied on a tangible medium, firmware, or hardware, including the structures disclosed in this specification and their structural equivalents, or in combinations of one or more of them. Implementations of the subject matter described in this specification can be implemented as one or more computer programs, e.g., one or more components of computer program instructions, encoded on computer storage medium for execution by, or to control the operation of, data processing apparatus. The program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can include a source or destination of computer program instructions encoded in an artificially-generated propagated signal. The computer storage medium can also be, or be included in, one or more separate physical components or media (e.g., multiple CDs, disks, or other storage devices, any other storage media described herein, etc.).

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements, and features discussed in connection with one implementation are not intended to be excluded from a similar role in other implementations.

The phraseology and terminology used herein is for the purpose of description and should not be regarded as limiting. The use of "including," "comprising," "having," "containing," "involving," "characterized by," "characterized in that," and variations thereof herein is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the terms "about" and "substantially" will be understood by persons of ordinary skill in the art and will vary to some extent depending upon the context in which they are used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations.

References to any act or element being based on any information, act, or element may include implementations where the act or element is based at least in part on any information, act, or element.

Any implementation disclosed herein may be combined with any other implementation or embodiment, and references to "an implementation," "some implementations," "one implementation," or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all the described terms. For example, a reference to "at least one of 'A' and 'B'"can include only 'A', only 'B', as well as both 'A' and 'B'. Such references used in conjunction with "comprising" or other open terminology can include additional items.

Where technical features in the drawings, detailed description, or any claim are followed by reference signs, the reference signs have been included to increase the intelligibility of the drawings, detailed description, and claims. Accordingly, neither the reference signs nor their absence has any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system, comprising:
an inlet channel that receives a target fluid flow comprising target particles;
an acoustophoresis device that receives the target fluid flow comprising the target particles from the inlet channel and moves the target particles from the target fluid flow to a buffer fluid flow comprising cargo particles;
an electroporation device downstream from the acoustophoresis device that receives the buffer fluid flow comprising the target particles and the cargo particles, and applies an electric field to the buffer fluid flow to cause a portion of the target particles in the buffer fluid flow to absorb a portion of the cargo particles;
a conductivity sensor coupled to an inlet of the electroporation device and configured to measure a conductivity of the buffer fluid flow received by the electroporation device and provide a signal indicating the conductivity;
an outlet channel that provides an output buffer fluid flow from the electroporation device; and a controller configured to receive the signal from the conductivity sensor and control a pump to adjust a flow rate of the target fluid flow into the inlet channel based on the conductivity.

2. The system of claim 1, wherein the acoustophoresis device comprises:

a central channel that receives the buffer fluid flow comprising the cargo particles from a source of buffer fluid and the target fluid flow from the inlet channel; and a piezoelectric transducer coupled to the central channel that causes the target particles to move from the target fluid flow to the buffer fluid flow in the central channel.

3. The system of claim 1, wherein the electroporation device comprises:

a central channel receiving the buffer fluid flow from the acoustophoresis device and a conductive buffer flow from a second channel; and an electrode electrically coupled to a portion of the central channel that provides the electric field.

4. The system of claim 1, wherein the target particles in the target fluid flow are lymphocytes, and the target fluid flow further comprises waste particles including at least one of red blood cells, granulocytes, or monocytes.

5. The system of claim 1, wherein the inlet channel is a first inlet channel, and further comprising:

a second inlet channel that receives an input fluid flow comprising waste particles and the target particles; and an acoustic separation device that receives the input fluid flow comprising the target particles and the waste particles from the second inlet channel and separates the input fluid flow into the target fluid flow comprising the target particles and a waste fluid flow comprising the waste particles.

6. The system of claim 5, wherein the waste fluid flow is transported via one or more waste channels to a waste reservoir, and the target fluid flow that exits from the acoustic separation device is transported via a second outlet channel into a target reservoir; and wherein the system further comprises a pump that transports the target fluid flow from the target reservoir to the acoustophoresis device via the second inlet channel.

7. The system of claim 1, further comprising:

the pump, wherein the pump transports the target fluid flow from an input reservoir to the acoustophoresis device via the inlet channel; and another pump that transports the buffer fluid flow comprising the target particles and the cargo particles from the acoustophoresis device to the electroporation device via an intermediate channel.

8. The system of claim 1, further comprising one or more holding reservoirs between two or more of the inlet channel, the acoustophoresis device, the electroporation device, or the outlet channel.

9. The system of claim 1, further comprising:

a separation device that receives the output buffer fluid flow from the outlet channel and separates enriched target particles in the output buffer fluid flow from waste particles in the output buffer fluid flow; and an output reservoir that receives the enriched target particles from the separation device.

10. The system of claim 1, wherein connections between two or more of the inlet channel, the acoustophoresis device, the electroporation device, or the outlet channel comprise at least one of poly-vinyl-chloride tubing or silicone tubing.

11. The system of claim 10, further comprising:

one or more fluid capacitors coupled with at least one of the connections, the one or more fluid capacitors configured to regulate a flow rate of at least one fluid in the system.

12. The system of claim 1, further comprising:

one or more sensors configured to transmit, to the controller, signals representing a density value of waste particles or the target particles in at least one of the target fluid flow, the buffer fluid flow, or the output buffer fluid flow.

13. The system of claim 1, further comprising:

one or more flow sensors that transmit, to the controller, one or more signals representing a flow rate of a fluid flowing through at least one of the inlet channel, the acoustophoresis device, the electroporation device, or the outlet channel.

* * * * *